(12) United States Patent
Johs et al.

(10) Patent No.: US 6,859,278 B1
(45) Date of Patent: Feb. 22, 2005

(54) MULTI-AOI-SYSTEM FOR EASY CHANGING ANGLES-OF-INCIDENCE IN ELLIPSOMETER, POLARIMETER AND REFLECTOMETER SYSTEMS

(75) Inventors: Blaine D. Johs, Lincoln, NE (US); Ping He, Lincoln, NE (US); Martin M. Liphardt, Lincoln, NE (US); Christopher A. Goeden, Lincoln, NE (US); John A. Woollam, Lincoln, NE (US); James D. Welch, Omaha, ME (US)

(73) Assignee: J.A. Woollam Co. Inc., Lincoln, NE (US)

( * ) Notice: Subject to any disclaimer, the term of this patent is extended or adjusted under 35 U.S.C. 154(b) by 402 days.

(21) Appl. No.: 10/050,802

(22) Filed: Jan. 15, 2002

Related U.S. Application Data

(60) Provisional application No. 60/287,784, filed on May 2, 2001, provisional application No. 60/263,874, filed on Jan. 25, 2001, and provisional application No. 60/261,243, filed on Jan. 16, 2001.

(51) Int. Cl.[7] .............................................. G01N 21/21
(52) U.S. Cl. ..................................................... 356/369
(58) Field of Search ................................ 356/364–369; 250/225

(56) References Cited

U.S. PATENT DOCUMENTS

| | | | |
|---|---|---|---|
| 3,874,797 A | 4/1975 | Hasai ........................ 356/118 |
| 4,053,232 A | 10/1977 | Dill et al. .................... 356/118 |
| 4,647,207 A | 3/1987 | Björk et al. ................. 356/369 |
| 4,668,086 A | 5/1987 | Redner ........................ 356/367 |
| 4,672,196 A | 6/1987 | Canino ........................ 250/225 |
| 5,229,833 A | 7/1993 | Stewart ....................... 356/364 |
| 5,329,357 A | 7/1994 | Bernoux et al. ............. 356/369 |
| 5,343,293 A | 8/1994 | Berger et al. ............... 356/369 |
| 5,410,409 A | 4/1995 | Ray ............................ 356/369 |
| 5,504,582 A | 4/1996 | Johs et al. ................... 356/369 |
| 5,521,706 A | 5/1996 | Green et al. ................ 356/369 |
| 5,581,350 A | 12/1996 | Chen et al. .................. 356/364 |
| 5,582,646 A | 12/1996 | Woollam et al. ............ 118/208 |
| 5,596,406 A | 1/1997 | Rosencwaig et al. ....... 356/327 |
| 5,666,201 A | 9/1997 | Johs et al. ................... 356/369 |
| 5,706,087 A | 1/1998 | Thompson et al. ......... 356/364 |
| 5,706,212 A | 1/1998 | Thompson et al. ......... 364/525 |
| 5,757,494 A | 5/1998 | Green et al. ................ 356/369 |
| 5,764,365 A | 6/1998 | Finarov ...................... 356/381 |
| 5,872,630 A | 2/1999 | Johs et al. ................... 356/369 |
| 5,929,995 A | * 7/1999 | Johs ........................... 356/369 |
| 5,963,327 A | 10/1999 | He et al. ..................... 356/369 |
| 6,034,777 A | 3/2000 | Johs et al. ................... 356/369 |
| 6,081,334 A | 6/2000 | Grimbergen et al. ....... 356/357 |
| 6,268,917 B1 | * 7/2001 | Johs ........................... 356/369 |
| 6,441,902 B1 | * 8/2002 | Hilfiker et al. .............. 356/369 |
| 6,456,376 B1 | * 9/2002 | Liphardt et al. ............ 356/369 |
| 6,483,586 B1 | * 11/2002 | Johs et al. ................... 356/369 |

OTHER PUBLICATIONS

An article by Johs, titled "Regression Calibration Method For Rotating Element Ellipsometers", which appeared in Thin Film Solids, vol. 234 in 1993.

A paper by Nijs & Silfhout, titled "Systematic and Random Errors in Rotating–Analyzer Ellipsometry", J. Opt. Soc. Am. A., vol. 5, No. 6, (Jun. 1988).

(List continued on next page.)

*Primary Examiner*—Hoa Q. Pham
(74) *Attorney, Agent, or Firm*—James D. Welch

(57) ABSTRACT

Disclosed is a system for enabling easy sequential setting of different Angles-of-Incidence of a beam of electromagnetic radiation to a surface of a sample system, and to regression based methodology for evaluating and compensating the effects of the presence of electromagnetic beam intercepting angle-of-incidence changing systems, including where desired, parameterization of calibration parameters.

19 Claims, 5 Drawing Sheets

OTHER PUBLICATIONS

An article by Jellison Jr. titled "Data Analysis for Spectroscopic Ellipsometry", Thin Film Solids, 234, (1993).

Papers of interest in the area by Azzam & Bashara; "Unified Analysis of Ellipsometry Errors Due to Imperfect Components Cell–Window Birefringence, and Incorrect Azimuth Angles", J. of the Opt. Soc. Am., vol 61, No. 5, (May 1971).

"Analysis of Systematic Errors in Rotating–Analyzer Ellipsometers", J. of the Opt. Soc. Am., vol. 64, No. 11, (Nov. 1974).

A paper by Straaher et al., titled "The Influence of Cell Window Imperfections on the Calibration and Measured Data of Two Types of Rotating Analyzer Ellipsometers", Surface Sci., North Holland, 96, (1980).

An article by Collins titled "Automated Rotating Element Ellipsometers: Calibration, Operation, and Real–Time Applications", Rev. Sci. Instrum. 61(8), Aug. 1990.

An article by Kleim et al. titled "Systematic Errors in Rotating–Compensator Ellipsometry" published in J. Opt. Soc. Am./vol. 11, No. 9, Sep. 1994.

* cited by examiner

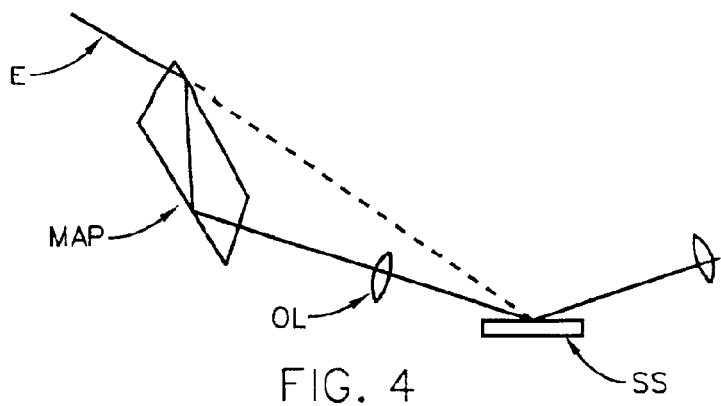
FIG. 4
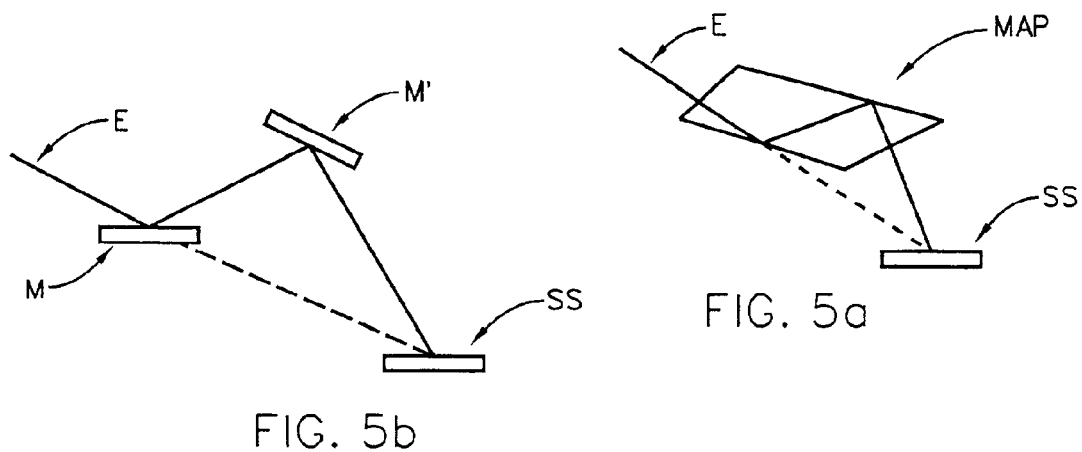
FIG. 5a
FIG. 5b
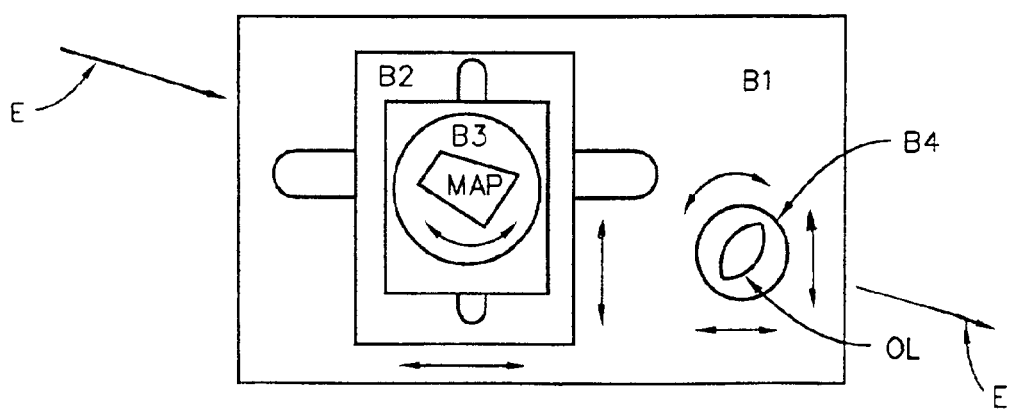
FIG. 6

3D VIEW OF ALL 4 MIRROR REFLECTIONS

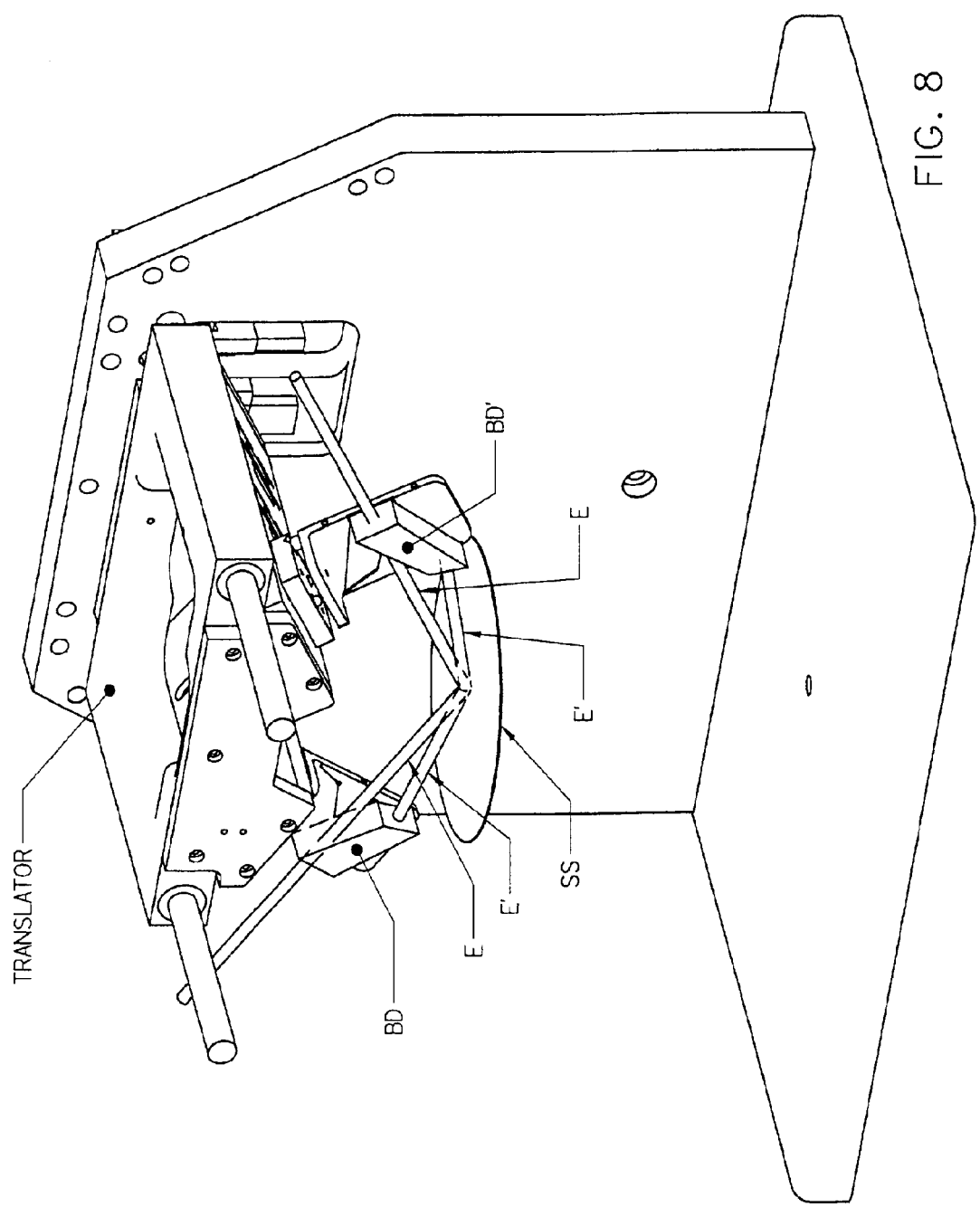

MULTI-AOI-SYSTEM FOR EASY CHANGING ANGLES-OF-INCIDENCE IN ELLIPSOMETER, POLARIMETER AND REFLECTOMETER SYSTEMS

This Application is a Continuation-In-Part of Provisional Applications Ser. No. 60/261,243 filed Jan. 16, 2001, and Ser. No. 60/263,874 filed Jan. 25, 2001, and Ser. No. 60/287,784 filed May 2, 2001.

TECHNICAL FIELD

The present invention relates to data acquisition from material system investigation systems such as ellipsometers, polarimeters, reflectometers, spectrophotometers and the like, and more particularly to systems for enabling easy sequential setting of different Angles-of-Incidence of a beam of electromagnetic radiation to a surface of a sample system, and to regression based methodology for evaluating and compensating the effects of the presence of electromagnetic beam intercepting angle-of-incidence changing systems, including where desired, parameterization of calibration parameters.

BACKGROUND

While present invention systems can be applied in any material system investigation system such as Polarimeter, Reflectometer, Spectrophotometer and the like Systems, an important application is in Ellipsometer Systems, whether monochromatic or spectroscopic. It should therefore be understood that Ellipsometry involves acquisition of sample system characterizing data at single or multiple Wavelengths, and at one or more Angle(s)-of-Incidence (AOI) of a Beam of Electromagnetic Radiation to a surface of the sample system. Ellipsometry is generally well described in a great many number of publications, one such publication being a review paper by Collins, titled "Automatic Rotating Element Ellipsometers: Calibration, Operation and Real-Time Applications", Rev. Sci. Instrum, 61(8) (1990).

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system:

$$TAN\ (\psi)e^{(i\Delta)} = r_p/r_s$$

Continuing, Ellipsometer Systems generally include a source of a beam of electromagnetic radiation, a Polarizer, which serves to impose a known, (typically linear), state of polarization on a beam of electromagnetic radiation, a. Stage for supporting a sample system, and an Analyzer which serves to select a polarization state in a beam of electromagnetic radiation after it has interacted with a material system, and pass it to a Detector System for analysis therein. As well, one or more Compensator(s) can be present and serve to affect a phase retardance between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because they do not demonstrate "Dead-Spots" where obtaining ellipsometric data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have a "Dead Spot" at PSI near 45 Degrees). The utility of Rotating Compensator Ellipsometer Systems should then be apparent. Another benefit provided by Rotating Compensator Ellipsometer Systems is that the Polarizer (P) and Analyzer (A) positions are fixed, and that provides benefit in that polarization state sensitivity to input and output optics during data acquisition is essentially non-existent. This enables relatively easy use of optic fibers, mirrors, lenses etc. for input/output.

While Data taken at one (AOI) and one or multiple wavelengths is often sufficient to allow ellipsometric characterization of a sample system, the results of Ellipsometric Investigation can be greatly enhanced by using multiple (AOI's) to obtain additional data sets. However, while it is relatively easy to provide Wavelength change without extensive difficult physical Ellipsometer System Orientation change, it is typically difficult to change the Angle-of-Incidence (AOI) that a Beam of Electromagnetic Radiation makes to a surface of a sample system. An (AOI) change requires that both the Source of the Electromagnetic Beam and the Detector must be re-positioned and aligned, and such is tedious and time consuming.

Further, it is to be understood that causing a polarized beam of electromagnetic radiation to interact with a sample system generally causes change in the ratio of the intensities of orthogonal components thereof and/or the phase shift between said orthogonal components. The same is generally true for interaction between any system component and a polarized beam of electromagnetic radiation. In recognition of the need to isolate the effects of an investigated sample system from those caused by interaction between a beam of electromagnetic radiation and system components other than said sample system, (to enable accurate characterization of a sample system per se.), this Specification incorporates by reference the regression procedure of U.S. Pat. No. 5,872, 630 in that it describes simultaneous evaluation of sample characterizing parameters such as PSI and DELTA, as well system characterizing parameters, and this Specification also incorporates by reference the Vacuum Chamber Window Correction methodology of U.S. Pat. No. 6,034,777 to account for phase shifts entered between orthogonal components of a beam of electromagnetic radiation, by present invention system multiangle prisms and/or lenses.

Another Patent which is incorporated hereinto by reference is No. 5,969,818 to Johs et al. Said 818 Patent describes a Beam Folding Optics System which serves to direct an electromagnetic beam via multiple reflections, without significantly changing the phase angle between orthogonal components therein. Briefly, two pairs of mirrors are oriented to form two orthogonally related planes such that the phase shift entered to an electromagnetic beam by interaction with the first pair of mirrors is canceled by interaction with the second pair.

Another Patents incorporated hereinto by reference is U.S. Pat. No. 5,757,494 to Green et al., in which is taught a method for extending the range of Rotating Analyzer/Polarizer ellipsometer systems to allow measurement of DELTA'S near zero (0.0) and one-hundred-eighty (180) degrees. Said Patent describes the presence of a window-like variable bi-refringent component which is added to a Rotating Analyzer/Polarizer ellipsometer system, and the application thereof during data acquisition, to enable the identified capability.

A Patent to Thompson et al. U.S. Pat. No. 5,706,212 teaches a mathematical regression based double Fourier series ellipsometer calibration procedure for application, primarily, in calibrating ellipsometers system utilized in infrared wavelength range. Bi-refringent window-like compensators are described as present in the system thereof, and discussion of correlation of retardations entered by sequentially adjacent elements which do not rotate with respect to one another during data acquisition is described therein.

A Patent to Woollam et al, U.S. Pat. No. 5,582,646 is disclosed as it describes obtaining ellipsometic data through windows in a vacuum chamber, utilizing other than a Brewster Angle of Incidence.

Patent to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to Rotating Analyzer ellipsometer systems.

Patent to Bernoux et al., U.S. Pat. No. 5,329,357 is identified as it describes the use of optical fibers as input and output means in an ellipsometer system.

A Patent to Finarov, U.S. Pat. No. 5,764,365 is disclosed as it describes a system for moving an ellipsometer beam over a large two-dimensional area on the surface of a sample system, which system utilizes beam deflectors.

A Patent to Berger et al., U.S. Pat. No. 5,343,293 describes an Ellipsometer which comprises prisms to direct an electromagnetic beam onto a sample system.

A Patent to Canino, U.S. Pat. No. 4,672,196 describes a system which allows rotating a sample system to control the angle of incidence of a beam of electromagnetic radiation thereonto. Multiple detectors are present to receive the resulting reflected beams.

A Patent to Bork et al., U.S. Pat. No. 4,647,207 describes an ellipsometer system in which reflecting elements are moved into the path of a beam of electromagnetic radiation.

U.S. Pat. No. 6,081,334 to Grimbergen et al. describes a system for detecting semiconductor end point etching including a means for scanning a beam across the surface of a substrate.

A Patent to Ray, U.S. Pat. No. 5,410,409 describes a system for scanning a laser beam across a sample surface.

U.S. Pat. No. 3,874,797 to Kasai describes means for directing a beam of electromagnetic radiation onto the surface of a sample using totally internally reflecting prisms.

U.S. Pat. No. 5,412,473 to Rosencwaig et al., describes a ellipsometer system which simultaneously provides an electromagnetic beam at a sample surface at numerous angles of incidence thereto.

A Patent to Chen et al., U.S. Pat. No. 5,581,350 is identified as it describes the application of regression in calibration of ellipsometer systems.

An article by Johs, titled "Regression Calibration Method For Rotating Element Ellipsometers", which appeared in Thin Film Solids, Vol. 234 in 1993 is also identified as it predates the Chen et al. Patent and describes an essentially similar approach to ellipsometer calibration.

A paper by Nijs & Silfhout, titled "Systematic and Random Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (September 1994) describes first order corrections for imperfections in windows and compensators in Rotating Compensator ellipsometers.

Other papers of interest in the area by Azzam & Bashara include one titled "Unified Analysis of Ellipsometry Errors Due to Imperfect Components Cell-Window Birefringence, and Incorrect Azimuth Angles", J. of the Opt. Soc. Am., Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al., titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

Also, a paper which is co-authored by the inventor herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

Even in view of the prior art, need remains for:

a simple to use system for enabling easy sequential setting of different angle-of-Incidence of a beam of electromagnetic radiation with respect to a surface of a sample system in ellipsometer, polarimeter, reflectometer, spectrophotometer and the like systems, without the accompanying need to move source and/or detector of electromagnetic radiation;

particularly where combined with an approach to account for any effects of the presence thereof, during evaluation of sample system PSI and DELTA values.

DISCLOSURE OF THE INVENTION

The disclosed invention system is primarily a means for enabling easy provision of multiple Angles-of-Incidence of a beam of electromagnetic radiation with respect to a sample system surface in material system investigation systems such as:

ellipsometer;

polarimeter;

reflectometer; and spectrophotometer;

which operate at at least one wavelength in at least one wavelength range, such as:

VUV;

UV;

Visible;

Infrared;

Far Infrared;

Radio Wave.

In use, a disclosed invention electromagnetic beam intercepting angle-of-incidence changing system is situated near a sample system such that its functional effects can be easily entered into and removed from the path of an electromagnetic beam. When functionally in the path of the electromagnetic beam the disclosed invention system elements intercept electromagnetic beam radiation on both the impinging and reflected side of the sample system. When the disclosed invention electromagnetic beam intercepting angle-of-incidence changing system is caused to be functionally in the path of the electromagnetic beam it acts, via such as total internal reflection within multiangle prisms or functional equivalents, (eg. reflection from a sequence of mirrors), to direct said electromagnetic beam at the sample system at a different Angle-of-Incidence than is the case if the electromagnetic beam simply directly approaches and reflects from the sample system surface, however, and importantly as it is what provides the utility of the disclosed invention, the electromagnetic beam is directed to substantially the same spot, (Spot "A" in FIGS. 1 and 2), on a sample system being investigated. That is, the same spot on a sample system surface is addressed regardless of the presence of a disclosed invention Angle-of-Incidence changing system in the pathway of the electromagnetic beam. Further, as the electromagnetic beam Locus beyond the disclosed invention Angle-of Incidence changing system is not changed by a disclosed invention Angle-of-Incidence changing system, the presence thereof in the path of an electromagnetic beam does not require any realignment of a Source of the electromagnetic beam, or Detector thereof. In addition, where a disclosed invention system is entered into the locus of an electromagnetic beam by physical motion, multiple disclosed invention electromagnetic beam intercepting angle-of-incidence changing systems can be present adjacent to one another such that each can, as desired by a user, be sequentially physically moved into place, and thereby provide the possibility of sequentially easily effecting multiple different Angles-of-Incidence. When multiple different disclosed invention Angle-of Incidence changing system(s) are utilized, they are distinguished by the presence of differently shaped Multiangle prisms, or functional equivalents thereof, therewithin. Note, however, that as is described later herein, some embodiments of the disclosed invention system are held stationary in position, and which electromagnetic beam enters a detector is controlled by shutter doors and/or control of the transmission/reflection properties of an internal surface of a multiangle prism.

In practical application, the disclosed invention can then be described as:

at least one electromagnetic beam intercepting angle-of-incidence changing system which comprises elements that are easily functionally entered into the locus of the electromagnetic beam on both sides of a sample system;

in functional combination with:

a material system investigation system comprising a source of electromagnetic radiation, a means for supporting a sample system, and a detector, such that in use a beam of electromagnetic radiation is provided by said source of electromagnetic radiation and is caused to reflect from a sample system placed on said means for supporting a sample system and enter said detector.

As mentioned, said at least one electromagnetic beam intercepting angle-of-incidence changing system, when caused to be functionally present in the path of an electromagnetic beam, serves to direct said electromagnetic beam onto substantially the same spot on the sample system as is the case where said at least one electromagnetic beam intercepting angle-of-incidence changing system is not so functionally present, but at an angle-of-incidence which is different than that which exists when said at least one electromagnetic beam intercepting angle-of-incidence changing system is not functionally present. Importantly, said at least one electromagnetic beam intercepting angle-of-incidence changing system does not effect, or require change of the locus of the electromagnetic beams outside said at least one electromagnetic beam intercepting angle-of-incidence changing system, on either side of said means for supporting a sample system, hence present systems eliminate the requirement that a material system investigating system comprise multiple sources and/or detectors, or that the position of the source of electromagnetic radiation and/or detector thereof be changed during use to effect said electromagnetic beam angle-of-incidence change.

At least one electromagnetic beam intercepting angle-of-incidence changing system can comprise, present on each side of said means for supporting a sample system, at least one selection from the groups consisting of:

multiple angle prism(s); and a system of mirrors;

said at least one electromagnetic beam intercepting angle-of-incidence changing system being slidably mounted to a guide element such that the functional presence thereof in the pathway of the locus of the electromagnetic beams on both sides of said means for supporting a sample system is effected by physical sliding motion of said at least one electromagnetic beam intercepting angle-of-incidence changing system along said guide element.

Another embodiment of the disclosed invention system provides that at least one electromagnetic beam intercepting angle-of-incidence changing system comprises:

a first multiangle prism on the incident side of said means for supporting a sample system and a second multiangle prism thereafter, said first and second multiangle prisms each having a first and a second side, each said multiangle prism presenting with first and second inner surfaces at said first and second sides respectively.

In this embodiment, the first and second sides of each multiangle prism have means for changing the properties of inner surface thereof from essentially transmissive to essentially reflective. Said means can be, for instance a voltage controlled liquid crystal array. In use, each multiangle prism is oriented such that an electromagnetic beam entering thereinto encounters said first or second inner surface thereof and either passes therethrough and progresses on to contact a sample system placed on said means for supporting a sample system; or reflects from said first or second inner surface thereof and then from said second or first inner surface thereof, respectively, and then progresses on to contact a sample system placed on said means for supporting a sample system. Said material system investigating system can further comprise at least one shutter door which can be opened to let the electromagnetic beam pass, or closed to block its passage, said at least one shutter door being positioned in the electromagnetic beam locus selected from the group consisting of:

defined by transmission through said first or second side of said first multiangle prism; and defined by reflection from said first or second side of said first multiangle prism;

said at least one shutter door being positioned between a first multiangle prism and the means for supporting a sample system and/or between said means for supporting a sample system and a second multiangle prism.

Another embodiment of a disclosed invention material system investigating system provides that at least one electromagnetic beam intercepting angle-of-incidence changing system comprises:

on first and second sides of said means for supporting a sample system, first and second, respectively, beam splitters.

Said first and second beam splitters each have the property that they pass approximately half, and reflect approximately half of a beam of electromagnetic radiation caused to be incident thereupon at an oblique angle to a surface thereof.

Said at least one electromagnetic beam intercepting angle-of-incidence changing system further comprises a first reflective means positioned to intercept the approximately half of the electromagnetic beam which reflects from said first beam splitter on the incident side of said means for supporting a sample system and direct it toward said means for supporting a sample system. Also present is a second reflective means positioned after said means for supporting a sample system to intercept an electromagnetic beam which reflects from a sample system placed on said means for supporting a sample system and direct it toward the second beam splitter. Said material system investigating system further comprises at least one shutter door which can be opened to let the electromagnetic beam pass, or closed to block its passage, said at least one shutter door being positioned in the pathway of the electromagnetic beam between which progresses along a locus selected from the group consisting of:

defined by passage through said first beam splitter; and defined by reflection from said first beam splitter;

on either side of said means for supporting a sample system. Typically four shutter doors will be present, two on each side of the means for supporting a sample system, said shutter doors being positioned in the loci of the electromagnetic beams which are most easily identified as those transmiting through and reflecting from the beam splitter on the incident side of the means for supporting a sample system, although said beams are continuous past sample system from which they reflect.

The material system investigating system including the disclosed invention can also include means for adjusting the orientation of at least one angle-of-incidence changing element in an electromagnetic beam intercepting angle-of-incidence changing system, optionally in simultaneous combination with included lenses positioned to focus a beam of electromagnetic radiation onto a sample system.

Continuing, as taught in U.S. Pat. No. 5,969,818 to Johs et al., (which is incorporated herein by reference), the disclosed invention at least one electromagnetic beam intercepting angle-of-incidence changing system can comprise, on first and/or second sides of said means for supporting a sample system, at least one system of mirrors, said at least one system of mirrors being comprised of:

a means for changing the propagation direction of an initial beam of electromagnetic radiation without significantly changing the phase angle between orthogonal components thereof, said means comprising two pairs of reflecting mirrors oriented so that said initial beam of electromagnetic radiation reflects from a first reflecting means in the first pair of reflecting means to a second reflecting means in said first pair of reflecting means, in a first plane; and such that the beam of electromagnetic radiation which reflects from the second reflecting means in said first pair of reflecting means reflects from the first reflecting means in said second pair of reflecting means to said second reflecting means in said second pair of reflecting means, in a second plane which is essentially orthogonal to said first plane; such that the direction of propagation of the beam of electromagnetic radiation reflected from the second reflecting means in said second pair of reflecting means is different from the propagation direction of the initial beam of electromagnetic radiation; the basis of operation being that changes entered between the orthogonal components by the first pair of reflective means is canceled by that entered by the second pair of reflective means.

It should be appreciated then that the disclosed invention is found primarily in the addition of disclosed invention Angle-of-Incidence changing system(s) to conventional material system investigation systems, and that the entering and/or removing procedure can be via physical motion of an angle-of-incidence changing system into and out of the locus of a beam of electromagnetic radiation, by operation of shutter doors statically placed in the locus of a beam of electromagnetic radiation, or by altering the properties of the inner surface of a multigangle prism statically placed to intercept a beam of electromagnetic radiation, to be transmissive or reflective. In any embodiment thereof, the utility of the disclosed invention is based upon the ease with which an angle-of-incidence of a beam of electromagnetic radiation to the surface of a sample system can be changed, (ie. typically attendant requirement for changing the position of a source and/or detector of electromagnetic radiation is not required).

The disclosed invention can also comprise the Mounting of a material system investigation system such as Ellipsometer, Polarimeter, Reflectometer or Spectrophotometer System, (with or without a disclosed invention angle-of-incidence changing system present), on an X-Y-Z Position Control System so it can be moved around the surface of a large area Sample, (Z is for focus). While non-limiting, an example is that very large, (eg. multiple feet by multiple feet), slabs of glass are these days coated with Indium-Tin-Oxide. It is necessary to "Map" the sample system to determine if the (ITO) thickness is even over its area. A solution is to place an Ellipsometer on a system that allows it to be moved in X-Y-Z directions, then sequentially move it, and take data, and repeat. (Note that if an Ellipsometer or Polarimeter or Reflectometer System is mounted to move in an X-Z or Y-Z plane, instead of the X-Y plane, then the Y or X, respectively, direction is for focus).

Further, it is to be understood that the disclosed invention incorporates by reference the regression based calibration methodology of U.S. Pat. No. 5,872,630 into its operation to simultaneously evaluate sample system characterizing parameters such as PSI and DELTA, as well as Ellipsometer or the like and disclosed invention system characterizing parameters, and also incorporates by reference the Window Correction and correlation breaking methodology of U.S. Pat. No. 6,034,777 to account for phase shifts entered between orthogonal components of a beam of electromagnetic radiation, by disclosed invention system multiangle prisms, system of mirrors and optional lenses, or functional equivalents.

Again, disclosed invention angle-of-incidence changing systems can be used in Polarimeter, Reflectometer, Spectrophotometer and the like Systems, as well as in Ellipsometer Systems, whether monochromatic or over a spectroscopic wavelength range.

To aid with Disclosure as to how the disclosed invention can be practiced, relevant material from U.S. Pat. Nos. 5,872,630 and 6,034,777 is included directly herewithin. In particular, while not limiting, a relevant ellipsometer system to which the disclosed invention system can be described as comprising:

a. a Source of a beam of electromagnetic radiation;

b. a Polarizer element;

c. optionally a compensator element;

d. (additional element(s));

e. a sample system;

f. (additional element(s));

g. optionally a compensator element;

h. an Analyzer element; and i. a Detector System;

wherein, in the context of the disclosed invention, said additional component(s) in d. and f. each comprise at least one electromagnetic beam intercepting angle-of-incidence changing system element which can be easily entered into the locus of the electromagnetic beam on both sides of said sample system, which at least one electromagnetic beam intercepting angle-of-incidence changing system elements serves to direct said electromagnetic beam onto substantially the same spot on the sample system as is the case where the said at least one electromagnetic beam intercepting angle-of-incidence changing system elements are not present, but at an angle-of-incidence which is different than that when said at least one electromagnetic beam intercepting angle-of-incidence changing system is not present. Said at least one electromagnetic beam intercepting angle-of-incidence changing system elements does not effect, or requiring change of, the locus of the electromagnetic beams outside said at least one electromagnetic beam intercepting angle-of-incidence changing system elements, on either side of a sample system, hence does not require change of position of the source of electromagnetic radiation and/or detector to effect change said angle-of-incidence. The sample system investigation system electromagnetic beam intercepting angle-of-incidence changing system can comprise multi-angle prisms and/or plurality of mirrors, and/or shutter doors and/or means for changing the characteristics of the internal surface of a multiangle prism etc.

Continuing, under the teachings of the 630 Patent, each of said components b.–i. of the ellipsometer system must be accurately represented by a mathematical model, along with a vector which represents a beam of electromagnetic radiation provided from said source of a beam electromagnetic radiation identified in a. above.

It is noted that various ellipsometer configurations provide that a Polarizer or Analyzer or Compensator(s) can be rotated during data acquisition, and are describe variously as Rotating Polarizer (RPE), Rotating Analyzer (RAE) and Rotating Compensator (RCE) Ellipsometer Systems.

The disclosed invention system then, is applied in a material system investigating system, (eg. ellipsometer; polarimeter; reflectometer; spectrophotometer or the like, operating in, for instance, a VUV, UV, Visible, Infrared, Far Infrared or Radio Wavelength range, and comprises a source of electromagnetic radiation, a means for supporting a sample system, and a detector, such that in use a beam of electromagnetic radiation is provided by said source of electromagnetic radiation and is caused to reflect from a sample system placed on said means for supporting a sample system and enter said detector, at an angle-of-incidence which can be set by said disclosed invention angle-of-incidence changing system.

The at least one electromagnetic beam intercepting angle-of-incidence changing system can comprise a selection from the group consisting of:

multiple angle prism(s);

multiple angle prism(s) including means for changing the characteristics of internal surfaces thereof;

a system of mirrors;

shutter doors;

on each side of said sample system.

As mentioned, the material system investigating system can be mounted to an X-Y-Z position control system and can be oriented to investigate a surface of a sample oriented in a horizontal or vertical or a plane thereinbetween.

A disclosed invention material system investigating system can include at least two multiple angle prisms at a location on at least one of said both sides of said sample system, and can include Lenses positioned to focus a beam of electromagnetic radiation onto a sample system. There can also be present means for adjusting the orientation of at least one multiangle prism, or functional equivalent, in a angle-of-incidence changing system, said means allowing adjusting the orientation of at least one lens alone or in fixed combination with an electromagnetic beam intercepting angle-of-incidence changing system multiangle prism or functional equivalent.

As already mentioned, the material system investigating system can be applied in a setting selected from the group consisting of:

in-situ; and ex-situ.

As generally described in the 630 Patent with focus on a method of calibrating a spectroscopic rotating compensator material system investigation system, a generalized method of calibrating a material system investigation system comprises the steps of:

a. providing a material system investigation system comprising a source of a polychromatic beam of electromagnetic radiation, a polarizer, a stage for supporting a sample system, an analyzer, a dispersive optics and at least one detector system which contains a multiplicity of detector elements, said material system investigation system optionally comprising at least one compensator(s) positioned at a location selected from the group consisting of:

before said stage for supporting a sample system, and after said stage for supporting a sample system, and both before and after said stage for supporting a sample system;

such that when said material system investigation system is used to investigate a sample system present on said stage for supporting a sample system, at least one of said analyzer or polarizer or at least one of said at least one compensator(s) is/are caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said sample system, pass through said analyzer and interact with said dispersive optics such that a multiplicity of essentially single wavelengths are caused to simultaneously enter a corresponding multiplicity of detector elements in said at least one detector system;

said material system investigating system further comprising at least one angle-of-incidence changing system which can be easily entered into the locus of the electromagnetic beam on both sides of said sample system, which at least one angle-of-incidence changing system serves to direct said electromagnetic beam onto substantially the same spot on the sample system as is the case where the said at least one angle-of-incidence changing system is not present, but at an angle-of-incidence which is different than that when said at least one angle-of-incidence changing system is not present, said at least one angle-of-incidence changing system not effecting, or requiring change of, the locus of the electromagnetic beams outside said at least one angle-of-incidence changing system, on either side thereof, hence does not require multiple sources and/or detectors or change of position of the source of electromagnetic radiation and/or detector to effect change said angle-of-incidence;

b. in conjunction with other steps, developing a mathematical model of said material system investigation system which comprises as calibration parameter variables such as polarizer azimuthal angle orientation, present sample system PSI, present sample system DELTA, compensator azimuthal angle orientation(s), matrix components of said compensator(s), analyzer azimuthal angle orientation, and angle of incidence changing system representations, which mathematical model is effectively a transfer function which enables calculation of electromagnetic beam intensity as a function of wavelength detected by a detector element, given intensity as a function of wavelength provided by said source of a polychromatic beam of electromagnetic radiation;

c. causing a polychromatic beam of electromagnetic radiation produced by said source of a polychromatic beam of electromagnetic radiation, to pass through said polarizer, interact with a sample system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through present compensator(s);

d. obtaining an at least two dimensional data set of intensity values vs. wavelength and a parameter selected from the group consisting of:
   angle-of-incidence of said polychromatic beam of electromagnetic radiation with respect to a present sample system,
   azimuthal angle rotation of one element selected from the group consisting of:
      said polarizer; and
      said analyzer;
      at least one of said at least one compensator(s);
   while at least one selection from the group consisting of said polarizer; and
      said analyzer;
      at least one of said at least one compensator(s);
   is caused to continuously rotate;

e. performing a mathematical regression of said mathematical model onto said at least two dimensional data set, thereby evaluating calibration parameters in said mathematical model; said regression based calibration procedure evaluated calibration parameters serving to compensate said mathematical model for non-achromatic characteristics and non-idealities: of said compensator(s), and for azimuthal angles of said polarizer, analyzer and compensator(s).

Said method of calibrating a material system investigation system can further comprise including calibration parameters for detector element image persistence and read-out non-idealities in the mathematical model, and further evaluating said calibration parameters for detector element image persistence and read-out non-idealities in said regression procedure.

Said method of calibrating a material system investigation system can include, in the step of developing a calibration parameter containing mathematical model of said spectroscopic rotating compensator ellipsometer system, the steps of providing a matrix representation of each of said polarizer, present sample system, said compensator(s), and said analyzer etc., and determining a mathematical transfer function relating electromagnetic beam intensity out to intensity in, as a function of wavelength, by multiplication of said matrices.

Said method of calibrating a material system investigation system can further comprise the step of parameterizing calibration parameters by representing variation as a function of a member of the group consisting of: (wavelength, angle-of-incidence of said polychromatic beam of electromagnetic radiation with respect to a present sample system, and azimuthal angle orientation of one element selected from the group consisting of: (said polarizer and said analyzer)), by a parameter containing mathematical equation, said parameters being evaluated during said mathematical regression.

Said method of calibrating a material system investigation system can preferably specifically include selecting calibration parameters which are parameterized, (such as polarizer azimuthal angle orientation, compensator azimuthal angle orientations), matrix components of said compensator(s), and analyzer azimuthal angle orientation), each as a function of -wavelength-.

Said method of calibrating a spectroscopic rotating compensator material system investigation system can involve using a sample system which is selected from the group consisting of: (open atmosphere with the spectroscopic rotating compensator material system investigation system being oriented in a "straight-through" configuration, and other than open atmosphere with the spectroscopic rotating compensator material system investigation system being oriented in a "sample-present" configuration).

Continuing, it must also be appreciated that when ellipsometer system components/elements are sequentially located adjacent to one another and are stationary with respect to one another, an ellipsometer "sees" the sum total thereof as a composite single element. For instance, if a sample system is present between two elements of a disclosed invention electromagnetic beam intercepting angle-of-incidence changing system, an ellipsometric investigation will provide a PSI and DELTA of the composite thereof. This is clearly not what is desired. In view of this it is presented that the methodology described in the 777 Patent, which is focused in application to correcting for phase shifts between orthogonal components of a polarized electromagnetic beam caused by its passing through vacuum chamber input and output windows, can be applied to compensate the effects of the presence of a disclosed invention electromagnetic beam intercepting angle-of-incidence changing system, as well. As insight to what is taught in the 777 Patent consider that in-situ application of ellipsometry to investigation of a sample system present in a vacuum chamber presents a challenge to users of ellipsometer systems in the form of providing a mathematical model for each of said input and output windows, and providing a method by which the effects of said windows can be separated from the effects of an investigated sample system. (Like a disclosed invention system, input and output windows in a vacuum chamber are structurally positioned by said vacuum chamber and are not rotatable with respect to a sample system present in said vacuum chamber in use, thus preventing breaking correlation between parameters in equations for sequentially adjacent input and output windows and an investigated sample system by an element rotation technique). While correlation of parameters in mathematical equations which describe the effects of groupings of elements, (such as a compensator and an optional element(s)), can be tolerable, correlation between parameters in the mathematical model of an investigated sample system and other elements in the ellipsometer system must be broken to allow obtaining accurate sample system representing PSI and DELTA values, emphasis added. That is to say that correlation between parameters in a equations in a mathematical model which describe the effects of a stationary compensator and a sequentially next window element, (eg. correlation between effects of elements c. and d. or between f. and g. identified above), on a beam of electromagnetic radiation might be tolerated to the extent that said correlation does not influence determination of sample system describing PSI and DELTA values, but the correlation between parameters in equations which describe the effects of ellipsometer system components (eg. a., b., c., d., f., g., h. and i. identified above), and equations which describe the effects of a present sample system (eq. element e. above), absolutely must be broken to allow the ellipsometer system to provide accurate PSI and DELTA values for said sample system.

The 777 Patent describes a method of accurately evaluating parameters in parameterized equations in a mathematical model of a system of spatially separated input and output windows, as applied in an ellipsometry or polarimeter setting. If read with terminology "electromagnetic beam intercepting angle-of-incidence changing system" or "multiangle prisms or functional equivalent" in the place of the terminology "windows" it is apparent that said 777 Patent teachings can be directly applied to a scenario wherein disclosed invention electromagnetic beam intercepting angle-of-incidence changing system elements and a sample system, with benefit. This is because the total internal reflectance in the prisms simply introduces a phase retardation between orthogonal components of the polarized beam, (ie. birefingence is demonstrated), just like as does a vacuum chamber window. Said 777 Patent parameterized equations enable, when parameters therein are properly evaluated, independent calculation of retardation entered by each of said input window and said output window between orthogonal components of a beam of electromagnetic radiation caused to pass through said input and output windows. (It is to be understood that at least one of said input and output windows is birefringent).

A method then, of accurately evaluating parameters in parameterized equations in a mathematical model of a system of spatially separated input and output electromagnetic beam intercepting angle-of-incidence changing system elements, said parameterized equations enabling, when parameters therein are properly evaluated, independent calculation of retardation entered by each of said input output electromagnetic beam intercepting angle-of-incidence changing system elements between orthogonal components of a beam of electromagnetic radiation caused to pass through said input and output electromagnetic beam intercepting angle-of-Incidence changing system elements, at least one of said input and output electromagnetic beam intercepting angle-of-incidence changing system elements being birefringent, comprises, in a functional order, the steps of:

a. providing spatially separated input and output electromagnetic beam intercepting angle-of-incidence changing system elements at least one of which input and output electromagnetic beam intercepting angle-of-incidence changing system elements demonstrates birefringence when a beam of electromagnetic radiation is caused to pass therethrough, and further providing a means for supporting a sample system positioned between said input and output electromagnetic beam intercepting angle-of-incidence changing system elements;

b. positioning an ellipsometer system source of electromagnetic radiation and an ellipsometer system detector system such that in use a beam of electromagnetic radiation provided by said-source of electromagnetic radiation is caused to pass through said input electromagnetic beam intercepting angle-of-incidence changing system element, interact with a sample system, in a plane of incidence thereto, and exit through said output electromagnetic beam intercepting angle-of-incidence changing system element and enter said detector system;

c. providing a sample system to said means for supporting a sample system, the composition of said sample system being sufficiently well known so that retardance entered thereby to a polarized beam of electromagnetic radiation of a given wavelength, which is caused to interact with said sample system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto;

d. in conjunction with other steps, providing a mathematical model for said ellipsometer system and said input and output electromagnetic beam intercepting angle-of-incidence changing system elements, which comprises separate parameterized equations for independently calculating retardance entered between orthogonal components of a beam of electromagnetic radiation caused to pass through each of said input and output electromagnetic beam intercepting angle-of-incidence changing system elements; such that where parameters in said mathematical model are properly evaluated, retardance entered between orthogonal components of a beam of electromagnetic radiation which passes through each of said input and output electromagnetic beam intercepting angle-of-incidence changing system elements, and further interacts with said sample system in a plane of incidence thereto can be independently calculated from said parameterized equations;

e. obtaining a spectroscopic set of ellipsometric data with said parameterizable sample system present on the means for supporting a sample system, utilizing a beam of electromagnetic radiation provided by said source of electromagnetic radiation, said beam of electromagnetic radiation being caused to pass through said input electromagnetic beam intercepting angle-of-incidence changing system element, interact with said parameterizable sample system in a plane of incidence thereto, and exit through said output electromagnetic beam intercepting angle-of-incidence changing system element and enter said detector system;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input electromagnetic beam intercepting angle-of-incidence changing system element, interact with said sample system in a plane of incidence thereto, and exit through said output electromagnetic beam intercepting angle-of-incidence changing system element;

to the end that application of said parameterized equations for each of said input and output electromagnetic beam intercepting angle-of-incidence changing system elements and sample system for which values of parameters therein have been determined in step f., enables independent calculation of retardance entered between orthogonal components of a beam of electromagnetic radiation by each of said input and output electromagnetic beam intercepting angle-of-incidence changing system elements, and said sample system, at given wavelengths in said spectroscopic set of ellipsometric data, said calculated retardance values for each of said input electromagnetic beam intercepting angle-of-incidence changing system element, output electromagnetic beam intercepting angle-of-incidence changing system element and sample system being essentially uncorrelated.

The step e. obtaining of a spectroscopic set of ellipsometric data involves obtaining spectroscopic data which is multidimensional in that at least one angle-of-incidence (AOI) is involved, thereby making the data set dependent on wavelength and the (AOI). And, it is also to be specifically understood that said "data set" includes the situation wherein two data sets are obtained, one for the case wherein the angle-of-incidence changing sytem is in place, and one where it is not, both said data sets being spectroscopic.

Said method preferably, in step f., involves simultaneous evaluation of parameters in said mathematical model parameterized equations for said parameterizable sample system, and for said input and output electromagnetic beam intercepting angle-of-incidence changing system elements, can be achieved by a square error reducing mathematical curve fitting procedure.

Further, said method, in step d., involves provision of a mathematical model for said ellipsometer system and said input and output electromagnetic beam intercepting angle-of-incidence changing systems and said parameterizable sample system, can involve, for each of said input and output electromagnetic beam intercepting angle-of-incidence changing system elements, providing separate parameterized mathematical model equations for retardance entered to each of said two orthogonal components of a beam of electromagnetic radiation caused to pass through said input and output electromagnetic beam intercepting angle-of-incidence changing system elements; at least one of said orthogonal components for each of said input and output electromagnetic beam intercepting angle-of-incidence changing systems being directed out of the plane of incidence of said electromagnetic beam onto said parameterizable sample system; such that calculation of retardation entered between orthogonal components of said beam of electromagnetic radiation, by said input electromagnetic beam intercepting angle-of-incidence changing system element is provided by comparison of retardance entered to each of said orthogonal components for said input electromagnetic beam intercepting angle-of-incidence changing system, and such that calculation of retardation entered between orthogonal components of said beam of electromagnetic radiation, by said output electromagnetic beam intercepting angle-of-incidence changing system element is provided by comparison of retardance entered to each of said orthogonal components for said output electromagnetic beam intercepting angle-of-incidence changing system element.

Said method, in step f., provides for simultaneous evaluation of parameters in said mathematical model parameterized equations for said parameterizable sample system, and for said input and output electromagnetic beam intercepting angle-of-incidence changing system elements, is preferably achieved by a square error reducing mathematical curve fitting procedure.

Said method, in step b., provides for positioning of an ellipsometer system source of electromagnetic radiation and an ellipsometer system detector system and typically includes positioning a polarizer between said source of electromagnetic radiation and said input electromagnetic beam intercepting angle-of-incidence changing system, and the positioning of an analyzer between said output electromagnetic beam intercepting angle-of-incidence changing systems and said detector system, and the step e. obtaining of a spectroscopic set of ellipsometric data typically involves obtaining data at a plurality of settings of at least one component selected from the group consisting of:

said analyzer; and said polarizer.

Said method, in the step of providing mathematical model parameterized equations for enabling independent calculation of retardance entered by said input and said output electromagnetic beam intercepting angle-of-incidence changing system elements and a sample system between orthogonal components of a beam of electromagnetic radiation, can, but need not necessarily, involve use of parameterized equations having a form selected from the group consisting of:

$$ret(\lambda)=K1+(K2/\lambda^2)+(K3/\lambda^4)$$

$$ret(\lambda)=(K1/\lambda)$$

$$ret(\lambda)=(K1/\lambda)*(1+(K2/\lambda^2))$$

$$ret(\lambda)=(K1/\lambda)*(1+(K2/\lambda^2)+(K3/\lambda^4)).$$

Said method can further involve in step a., the providing of spatially separated input and output electromagnetic beam intercepting angle-of-incidence changing system elements which are mounted on an X, Y, Z orientation control system.

Another recitation of a method of accurately evaluating parameters in parameterized equations in a mathematical model of a system of spatially separated input and output electromagnetic beam intercepting angle-of-incidence changing system elements, which parameterized equations enable, when parameters therein are properly evaluated, independent calculation of retardation entered by each of said input electromagnetic beam intercepting angle-of-incidence changing system element and said output electromagnetic beam intercepting angle-of-incidence changing system to at least one orthogonal component(s) of a beam of electromagnetic radiation caused to pass through said input and output electromagnetic beam intercepting angle-of-incidence changing system elements, at least one of said input and output electromagnetic beam intercepting angle-of-incidence changing systems being birefringent, comprises, in a functional order, the steps of:

a. providing spatially separated input and output electromagnetic beam intercepting angle-of-incldence changing systems, at least one of said input and output electromagnetic beam intercepting angle-of-Incidence changing system elements demonstrating birefringence when a beam of electromagnetic radiation is caused to pass therethrough, there being a means for supporting a sample system positioned between said input and output electromagnetic beam intercepting angle-of-incidence changing system elements;

b. positioning an ellipsometer system source of electromagnetic radiation and an ellipsometer system detector system such that in use a beam of electromagnetic radiation provided by said source of electromagnetic radiation is caused to pass through said input electromagnetic beam intercepting angle-of-incidence changing system element, interact with a sample system, in a plane of incidence thereto, and exit through said output electromagnetic beam intercepting angle-of-incidence changing system element and enter said detector system;

c. providing a sample system to said means for supporting a sample system;

d. in combination with the other steps, providing a mathematical model for said ellipsometer system and said input and output electromagnetic beam intercepting angle-of-incidence changing system elements and said sample system, comprising, for each of said input electromagnetic beam intercepting angle-of-incidence changing system and said output electromagnetic beam intercepting angle-of-incidence changing system element, at least one parameterized equations for retardance for at least one orthogonal component in a beam of electromagnetic radiation provided by said source of electromagnetic radiation, which at least one orthogonal component is directed out-of-a-plane of incidence which said electromagnetic beam makes with said sample system in use, such that retardation entered to said out-of-plane orthogonal component can, for each of said input and output electromagnetic beam intercepting angle-of-incidence changing system, be separately calculated by said parameterized equations, where parameters in said parameterized equations are properly evaluated;

e. obtaining a spectroscopic set of ellipsometric data with said sample system present on the means for supporting a sample system, utilizing a beam of electromagnetic radiation provided by said source of electromagnetic radiation, said beam of electromagnetic radiation being caused to pass through said input electromagnetic beam intercepting angle-of-incidence changing system element, interact with said sample system in a plane of incidence thereto, and exit through said output electromagnetic beam intercepting angle-of-incidence changing system, and enter said detector system;

f. by utilizing said mathematical model provided in step d. and said spectroscopic set of ellipsometric data obtained in step e., simultaneously evaluating sample system DELTA'S in correlation with in-plane orthogonal component retardation entered to said beam of electromagnetic radiation by each of said input and output electromagnetic beam intercepting angle-of-incidence changing system elements, and parameters in said mathematical model parameterized equations for out-of-plane retardance entered by said input electromagnetic beam intercepting angle-of-incidence changing system element and said output electromagnetic beam intercepting angle-of-incidence changing system element to a beam of electromagnetic radiation caused to pass through said input electromagnetic beam intercepting angle-of-incidence changing system, interact with said sample system in said plane of incidence thereto, and exit through said output electromagnetic beam intercepting angle-of-incidence changing system element;

to the end that application of said parameterized equations for out-of-plane retardance entered by said input electromagnetic beam intercepting angle-of-incidence changing system element and said output electromagnetic beam intercepting angle-of-incidence changing system element to a beam of electromagnetic radiation caused to pass through said input electromagnetic beam intercepting angle-of-incidence changing system, interact with said sample system in said plane of incidence thereto, and exit through said output electromagnetic beam intercepting angle-of-incidence changing system element, for which values of parameters therein are determined in step f., enables independent calculation of retardance entered to said out-of-plane orthogonal component of a beam of electromagnetic radiation by each of said input and output electromagnetic beam intercepting angle-of-incidence changing systems.

Said method, in step f. can involve simultaneous evaluation of parameters in said mathematical model parameterized equations for calculation of retardance entered to said out-of-plane orthogonal component of a beam of electromagnetic radiation by each of said input and output electromagnetic beam intercepting angle-of-incidence changing system element and said correlated sample system DELTA'S and retardance entered to said in-plane orthogonal component of a beam of electromagnetic radiation by each of said input and output electromagnetic beam intercepting angle-of-incidence changing system elements, by a square error reducing mathematical curve fitting procedure.

Said method of accurately evaluating parameters in parameterized equations in a mathematical model of a system of spatially separated input and output electromagnetic beam intercepting angle-of-incidence changing system elements, can further comprise the steps of:

g. providing a parameterized equation for retardation entered by said sample system to the in-plane orthogonal component of a beam of electromagnetic radiation, and as necessary similar parameterized equations for retardation entered by each of said input and output electromagnetic beam intercepting angle-of-incidence changing system elements to the in-plane orthogonal component of a beam of electromagnetic radiation; and h. by utilizing said parameterized mathematical model provided in step d. and said spectroscopic set of ellipsometric data obtained in step e., simultaneously evaluating parameters in said mathematical model parameterized equations for independent calculation of retardance entered in-plane by said sample system and by said input electromagnetic beam intercepting angle-of-incidence changing system element and said output electromagnetic beam intercepting angle-of-incidence changing system element such that the correlation between sample system DELTA'S and the retardance entered by said in-plane orthogonal component of a beam of electromagnetic radiation by each of said input and output electromagnetic beam intercepting angle-of-incidence changing systems, at given wavelengths in said spectroscopic set of ellipsometric data, is broken;

to the end that application of said parameterized equations for each of said input electromagnetic beam intercepting angle-of-incidence changing system element, output electromagnetic beam intercepting angle-of-incidence changing system and sample system for which values of parameters therein have been determined in step h., enables independent calculation of retardance entered to both said out-of-plane and said in-plane orthogonal components of a beam of electromagnetic radiation by each of said input and output electromagnetic beam intercepting angle-of-incidence changing systems, and retardance entered by said sample system to said in-plane orthogonal component of said beam of electromagnetic radiation, at given wavelengths in said spectroscopic set of ellipsometric data.

Said method, in step h., can involve simultaneous evaluation of parameters in said mathematical model parameterized equations for said in-plane retardation entered by said parameterized sample system, and said input and output electromagnetic beam intercepting angle-of-incidence changing system elements, is achieved by a square error reducing mathematical curve fitting procedure.

Said method, can further comprise the alternative steps of:

g. removing the sample system from said means for supporting a sample system positioned between said input and output electromagnetic beam intercepting angle-of-incidence changing systems, and positioning in its place an alternative sample system for which a parameterized equation for calculating in-plane retardance entered to a beam of electromagnetic radiation, can be provided;

h. providing a parameterized equation for retardation entered in-plane to an orthogonal component of a beam of electromagnetic radiation by said alternative sample system which is then positioned on said means for supporting a sample system positioned between said input and output electromagnetic beam intercepting angle-of-incidence changing system elements, and as necessary similar parameterized equations for retardation entered by each of said input and output electromagnetic beam intercepting angle-of-incidence changing systems to the in-plane orthogonal component of a beam of electromagnetic radiation;

i. obtaining a spectroscopic set of ellipsometric data with said alternative sample system present on the means for supporting a sample system, utilizing a beam of electromagnetic radiation provided by said source of electromagnetic radiation, said beam of electromagnetic radiation being caused to pass through said input electromagnetic beam intercepting angle-of-incidence changing system element, interact with said alternative sample system in a plane of incidence thereto, and exit through said output electromagnetic beam intercepting angle-of-incidence changing system element and enter said detector system;

j. by utilizing said parameterized mathematical model for said input electromagnetic beam intercepting angle-of-incidence changing system element, and said output electromagnetic beam intercepting angle-of-incidence changing system element, provided in step d. and said parameterized equation for retardation entered by said alternative sample system provided in step h., and said spectroscopic set of ellipsometric data obtained in step i., simultaneously evaluating parameters in said mathematical model parameterized equations for independent calculation of retardance entered to an in-plane orthogonal component of said beam of electromagnetic radiation by said alternative sample system and by said input electromagnetic beam intercepting angle-of-incidence changing system element and said output electromagnetic beam intercepting angle-of-incidence changing system element, such that correlation between DELTA'S entered by said alternative sample system and retardance entered by said in-plane orthogonal component of said beam of electromagnetic radiation, by each of said input and output electromagnetic beam intercepting angle-of-incidence changing system elements, at given wavelengths in said spectroscopic set of ellipsometric data, is broken, said simultaneous evaluation optionally providing new values for parameters in parameterized equations for calculation of retardance entered in said out-of-plane components of said beam of electromagnetic radiation by each of said input electromagnetic beam intercepting angle-of-incidence changing system element and said output electromagnetic beam intercepting angle-of-incidence changing system element;

to the end that application of said parameterized equations for each of said input electromagnetic beam intercepting angle-of-incidence changing system element, output electromagnetic beam intercepting angle-of-incidence changing system and alternative sample system, for each of which values of parameters therein have been determined in step j., enables independent calculation of retardance entered to both said out-of-plane and said in-plane orthogonal components of a beam of electromagnetic radiation by each of said input electromagnetic beam intercepting angle-of-incidence changing system and said output electromagnetic beam intercepting angle-of-incidence changing system element, and retardance entered by said alternative sample system to said in-plane orthogonal component of a beam of electromagnetic radiation, at given wavelengths in said spectroscopic set of ellipsometric data.

Said method, in step j., can involve simultaneous evaluation of parameters in said mathematical model parameterized equations for said in-plane retardation entered by said parameterized sample system, and at least said in-plane input electromagnetic beam intercepting angle-of-incidence changing system element and output electromagnetic beam intercepting angle-of-incidence changing system element, by a square error reducing mathematical curve fitting procedure.

Said method, in step b., can involve positioning of an ellipsometer system source of electromagnetic radiation and an ellipsometer system detector system including positioning a polarizer between said source of electromagnetic radiation and said input electromagnetic beam intercepting angle-of-incidence changing system, and the positioning of an analyzer between said output electromagnetic beam intercepting angle-of-incidence changing system and said detector system, and in step e., the obtaining of a spectroscopic set of ellipsometric data involves obtaining data at a plurality of settings of at least one component selected from the group consisting of:

said analyzer; and said polarizer.

Said method, in the step of providing separate parameterized mathematical model parameterized equations for enabling independent calculation of out-of-plane retardance entered by said input and said output electromagnetic beam intercepting angle-of-incidence changing system elements to said beam of electromagnetic radiation caused to pass through said input and output electromagnetic beam intercepting angle-of-incidence changing system elements, can involve parameterized equations having a form selected from the group consisting of:

$$ret(\lambda)=K1+(K2/\lambda^2)+(K3/\lambda^4)$$

$$ret(\lambda)=(K1/\lambda)$$

$$ret(\lambda)=(K1/\lambda)*(1+(K2/\lambda^2))$$

$$ret(\lambda)=(K1/\lambda)*(1+(K2/\lambda^2))+(K3/\lambda^4)).$$

Said method, in the step of providing separate parameterized mathematical model parameterized equations for retardance entered to the out-of-plane and in-plane orthogonal components of a beam of electromagnetic radiation caused to pass through said input and output electromagnetic beam intercepting angle-of-incidence changing system elements, thereby enabling independent calculation of out-of-plane and in-plane retardance entered by said input and said output electromagnetic beam intercepting angle-of-incidence changing system elements to out-of-plane and in-plane orthogonal components of a beam of electromagnetic radiation caused to pass through said input and output electromagnetic beam intercepting angle-of-incidence changing system elements, and the step of providing a parameterized equation for in-plane retardance entered by interaction of said bean of electromagnetic radiation with said sample system can involve, for each input and output electromagnetic beam intercepting angle-of-incidence changing systems orthogonal retardation component and for said sample system retardation, parameterized equations having a form selected from the group consisting of:

$$ret(\lambda)=K1+(K2/\lambda^2)+(K3/\lambda^4)$$

$$ret(\lambda)=(K1/\lambda)$$

$$ret(\lambda)=(K1/\lambda)*(1+(K2/\lambda^2))$$

$$ret(\lambda)=(K1/\lambda)*(1+(K2/\lambda^2)+(K3/\lambda^4)).$$

Said method, in step a., can involve providing of spatially separated input and output electromagnetic beam intercepting angle-of-incidence changing system elements involves providing input and output electromagnetic beam intercepting angle-of-incidence changing system elements which are mounted on an X, Y, Z orientation control system.

Any recited method of accurately evaluating parameters in parameterized equations in a mathematical model of a system of spatially separated input and output electromagnetic beam intercepting angle-of-incidence changing system elements can further involve, in a functional order:

fixing evaluated parameter values in mathematical model parameterized equations, for each of said input electromagnetic beam intercepting angle-of-incidence changing system element and output electromagnetic beam intercepting angle-of-incidence changing system element, such that said parameterized equations allow independent determination of retardation entered between orthogonal components of a beam of electromagnetic radiation caused to pass through said input and output electromagnetic beam intercepting angle-of-incidence changing system elements; and causing an unknown sample system to be present on said means for supporting a sample system;

obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said input electromagnetic beam intercepting angle-of-incidence changing system element, interact with said alternative sample system in a plane of incidence thereto, and exit through said output electromagnetic beam intercepting angle-of-incidence changing system element and enter said detector system; and by utilizing said mathematical model for said input electromagnetic beam intercepting angle-of-incidence changing system and said output electromagnetic beam intercepting angle-of-incidence changing system element in which parameter values in mathematical model parameterized equations, for each of said input electromagnetic beam intercepting angle-of-incidence changing system element and output electromagnetic beam intercepting angle-of-incidence changing system have been fixed, simultaneously evaluating PSI'S and uncorrelated DELTA'S parameters for said unknown sample system, with a preferred practice involving simultaneous evaluation of PSI'S and DELTA'S for said unknown sample by a square error reducing mathematical curve fitting procedure.

It should also be appreciated that in any method of accurately evaluating parameters in parameterized equations in a mathematical model of a system of spatially separated input and output electromagnetic beam intercepting angle-of-incidence changing system elements, a step of providing spatially separated input and output electromagnetic beam intercepting angle-of-incidence changing system elements, wherein at least one of said input and output electromagnetic beam intercepting angle-of-incidence changing system elements demonstrates birefringence when a beam of electromagnetic radiation is caused to pass therethrough, can involve one electromagnetic beam intercepting angle-of-incidence changing system element which is not birefringent. Further, said at least one electromagnetic beam intercepting angle-of-incidence changing system element which is not birefringent can be essentially a surrounding ambient.

In any method of accurately evaluating parameters in parameterized equations in a mathematical model of a system of spatially separated input and output electromagnetic beam intercepting angle-of-incidence changing system elements, positioning of an ellipsometer system source of electromagnetic radiation and an ellipsometer system detector system can include positioning additional elements between said source of electromagnetic radiation and said input electromagnetic beam intercepting angle-of-incidence changing system element, and/or between said output electromagnetic beam intercepting angle-of-incidence changing system element and said detector system, and obtaining of a spectroscopic set of ellipsometric data obtained at a plurality of settings of at least one of said additional components.

Any method of accurately evaluating parameters in parameterized equations in a mathematical model of a system of spatially separated input and output electromagnetic beam intercepting angle-of-incidence changing system element can further involve, in a functional order:

fixing evaluated parameter values in mathematical model parameterized equations, for each of said input electromagnetic beam intercepting angle-of-Incidence changing system element and output electromagnetic beam intercepting angle-of-incidence changing system element, such that said parameterized equations allow independent determination of retardation entered between orthogonal components of a beam of electromagnetic radiation caused to pass through said input and output electromagnetic beam intercepting angle-of-incidence changing system element; and causing an unknown sample system to be present on said means for supporting a sample system;

obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said input electromagnetic beam intercepting angle-of-incidence changing system element, interact with said alternative sample system in a plane of incidence thereto, and exit through said output electromagnetic radiation being caused to pass through said input electromagnetic beam and enter said detector system; and by utilizing said mathematical model for said input electromagnetic beam intercepting angle-of-incidence changing system and said output electromagnetic beam intercepting angle-of-incidence changing system element in which parameter values in mathematical model parameterized equations, for each of said input electromagnetic beam intercepting angle-of-incidence changing system element and output electromagnetic beam intercepting angle-of-incidence changing system have been fixed, simultaneously evaluating ellipsometric ALPHA'S and BETA'S for said unknown sample system;

applying transfer functions to said simultaneously evaluated ALPHA'S and BETA'S for said unknown sample system to the end that a data set of effective PSI's and DELTA's for a combination of said electromagnetic beam intercepting angle-of-incidence changing system element and said sample system is provided;

providing a mathematical model for said combination of said electromagnetic beam intercepting angle-of-incidence changing system and said sample system which separately accounts for the retardation effects of the presence of said electromagnetic beam intercepting angle-of-incidence changing system element and said sample system by parameterized equations; and by utilizing said mathematical model for said combination of said electromagnetic beam intercepting angle-of-incidence changing system element and said sample system which separately accounts for the effects of the presence of at least said electromagnetic beam intercepting angle-of-incidence changing system by parameterized equations; and said data set of effective PSI's and DELTA's for a combination of said electromagnetic beam intercepting angle-of-incidence changing system and said sample system, simultaneously evaluating actual PSI's and DELTA's for said unknown sample system per se.

Said method, can involve, in the step of providing a mathematical model for said combination of said electromagnetic beam intercepting angle-of-incidence changing system elements and said sample system which separately accounts for the retardation effects of the presence of said input and output electromagnetic beam intercepting angle-of-incidence changing system elements and said sample system by parameterized equations, providing for the effects of handedness, and again preferred practice provides that evaluation of actual PSI's and DELTA's is achieved by a square error reducing mathematical curve fitting procedure. (Note, ellipsometric ALPHA AND BETA factors are described by Eqs. 2 and 3 in U.S. Pat. No. 5,757,494 to Green et al., which is incorporated hereinto by reference).

Again, it is to be understood that as regards any recited methodology, the obtaining of a spectroscopic set of ellipsometric data can involve obtaining spectroscopic data which is multidimensional in that at least one angle-of-incidence (AOI) is involved, thereby making the data set dependent on wavelength and the (AOI). And, it is also to be specifically understood that said "data set" includes the situation wherein the data set comprises what could be termed two effective data sets, one for the case wherein the angle-of-incidence (AOI) changing sytem is in place, and one where it is not, both said data sets being spectroscopic.

The disclosed invention will be better understood by reference to the Detailed Description Section of this Disclosure, with appropriate reference being has to the Drawings.

SUMMARY OF THE INVENTION

A primary purpose and/or objective of the disclosed invention is to teach a system for enabling easy sequential setting of different Angles-of-Incidence of a beam of electromagnetic radiation to a surface of a sample system, in material system investigation systems such as ellipsometers, polarimeters, reflectometers, spectrophotometers and the like systems.

Another purpose and/or objective of the disclosed invention is to teach a regression based methodology for evaluating and compensating the effects of the presence electromagnetic beam intercepting angle-of-incidence changing systems, including where desired, parameterization of calibration parameters.

Other purposes and/or objectives will become obvious from a reading of the Specification and claims.

BRIEF DESCRIPTION OF THE DRAWINGS

FIG. 4 shows Multiangle Prisms (MAP) comprise a disclosed invention electromagnetic beam intercepting angle-of-incidence changing system on right and left sides thereof.

FIG. 5a shows how a Multiangle Prism (MAP) changes the pathway of an Electromagnetic Beam by Total Internal Reflection therewithin.

FIG. 5b shows how a plurality of Mirrors can change the pathway of an Electromagnetic Beam by Reflection therefrom.

FIG. 6 shows a side elevational view of an adjustable mounting means for a Multiangle Prism (MAP), and optionally an Optical Lens (OL).

FIG. 8 shows a Three-Dimensional view of a disclosed invention system in the region a Sample System as demonstrated in FIG. 2.

DETAILED DESCRIPTION

Figure 1:
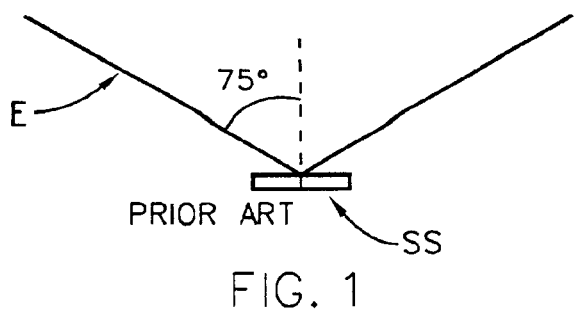
FIG. 1 shows a Front View of a Conventional Ellipsometer, Polarimeter or Reflectometer System with an Electromagnetic Beam shown approaching and reflecting from a sample system at an (AOI) of, for instance, 75 degrees.
Figure 2:
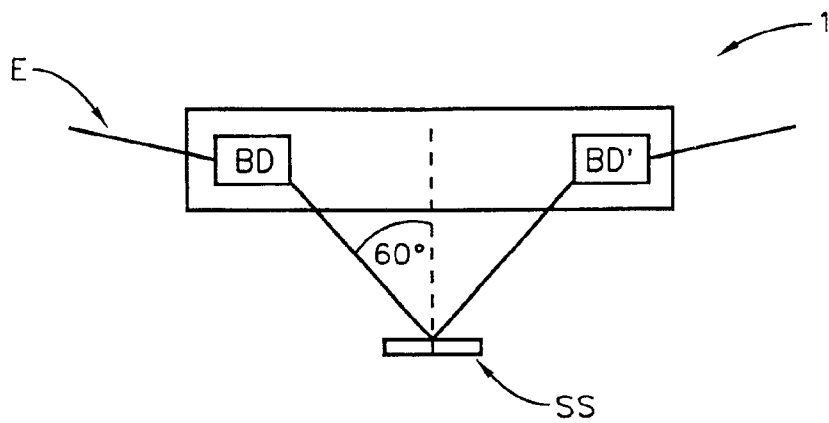
FIG. 2 shows that the (AOI) is changed to, for instance, 60 degrees when a Present Invention System (1) is placed in the pathway of the Electromagnetic Beam.
Figure 3A:
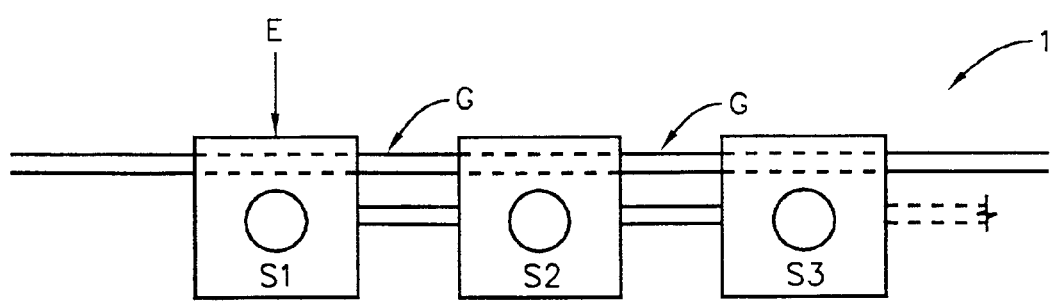
FIG. 3a shows a Side View of Present Invention System (s) (S1) (S2) (S3) mounted on a Guide (G) upon which they can be slid right and left. Present Invention System (S1) is shown slid into position to intercept Electromagnetic Beam (E).
Figure 3B:
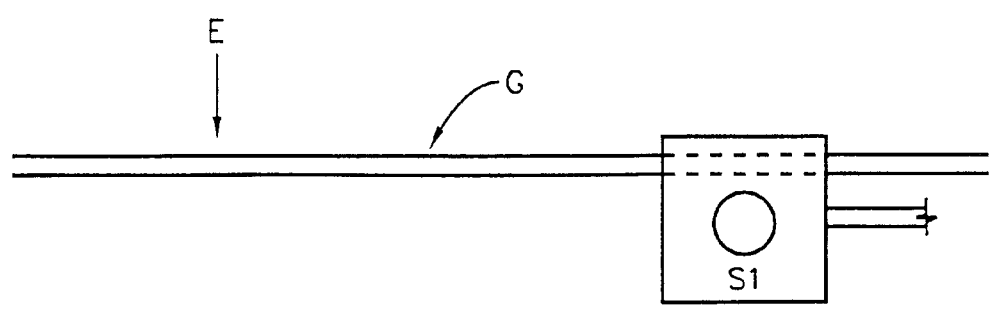
FIG. 3b shows a Side View of the system shown in FIG. 3a with Present Invention System(s) (S1) (S2) (S3) slid to the right therein such that none thereof intercepts Electromagnetic Beam (E).

FIG. 1 shows a Front View of a Material System Investigating System, (eg. Ellipsometer, Polarimeter, Reflectometer or Spectrophotometer System), with an Electromagnetic Beam shown approaching and reflecting from a Sample System (SS) at an (AOI) of, for instance, 75 degrees with respect to normal. FIG. 2 shows that the (AOI) is changed to, for instance, 60 degrees with respect to normal when a disclosed invention electromagnetic beam intercepting angle-of-incidence changing system (1) is placed in the pathway of the Electromagnetic Beam. FIG. 3a shows a Side View of a disclosed invention electromagnetic beam intercepting angle-of-incidence changing system mounted on a Guide (G) upon which they can be slid right and left. The location of a Materials System Investigating System with respect to the disclosed invention electromagnetic beam (E) intercepting angle-of-incidence changing system is indicated by (E), which is the same (E) indicated in FIGS. 1 and 2. Referral to FIGS. 3a and 3b shows that a sliding motion to the left will place a disclosed invention electromagnetic beam intercepting angle-of-incidence changing system (S1) (S2) (S3) in the pathway of an Ellipsometer System Electromagnetic Beam (E), (see FIG. 3a), and sliding disclosed invention electromagnetic beam intercepting angle-of-incidence changing system to the right moves them out of the Electromagnetic Beam, (see FIG. 3b). (Note right and left in FIGS. 3a and 3b correspond to a perpendicular to the plane of the surface of the paper in FIGS. 1 and 2.

FIG. 4 shows a Multiangle Prism (MAP) in a disclosed invention Electromagnetic Beam (E) intercepting Angle-of-Incidence changing system (1), on the left side thereof, (as indicated (BD) in FIG. 2). Note that the orientation of the (MAP) increases the (AOI) in FIG. 4, whereas in FIG. 2, (and 5a), the (MAP) is oriented to decrease the (AOI). FIG. 5a shows how a Multiangle Prism (MAP) changes the pathway of an Electromagnetic Beam by Total Internal Reflection therewithin. The shapes and materials which characterize the prisms can be designed and selected to cause the (desired (AOI) change, as well as effect phase shifts entered by total internal reflections to be stable, or at least have small sensitivity to changes in (AOI). Polymer for Far IR, Silicon or Germanium for IR, and Quartz for UV, VIS-NIR or CaF for VUV, for instance, can be utilized. And note that a two or more Multiangle Prisms can be present on at least one side of the sample system, to provide an (AOI) not possible where only one is present. FIG. 5b shows a plurality of mirrors (M) (M') can also form disclosed invention electromagnetic beam intercepting angle-of-incidence changing system. FIG. 4 also shows Optional Lenses (OL) can be positioned to focus a beam of electromagnetic radiation onto a spot on a sample system. Said Optional Lenses (OL) can be independently mounted, or affixed to the Multiangle Prisms (MAP). Note, it is possible to have two "Present Invention Systems" which provide the same AOI, one having Optional Lenses for focusing present, and the other not.

Figure 5C:
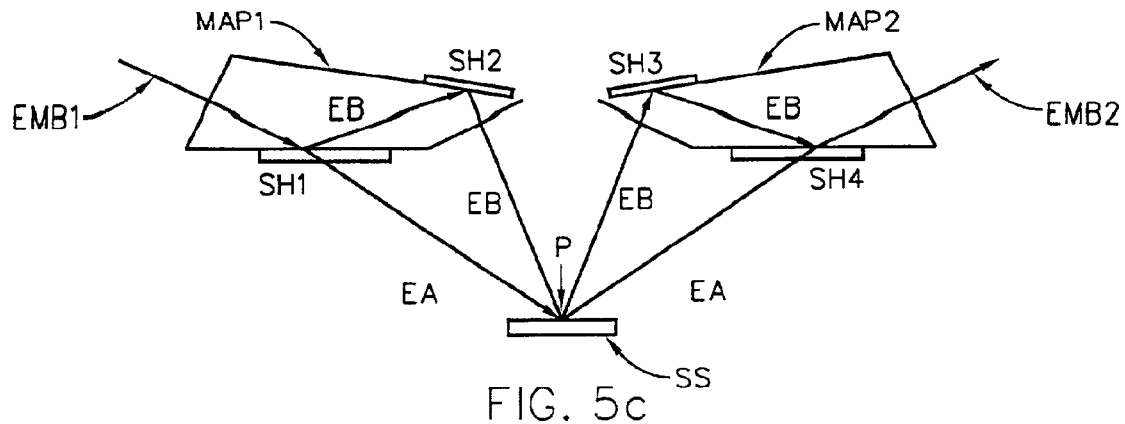
FIG. 5c shows additional configurations of Multiple Angle Prisms (MAP1) and (MAP2) which have Shutters (SH1) & (SH2), and (SH3) & (SH4) respectively present thereupon.
Figure 5D:
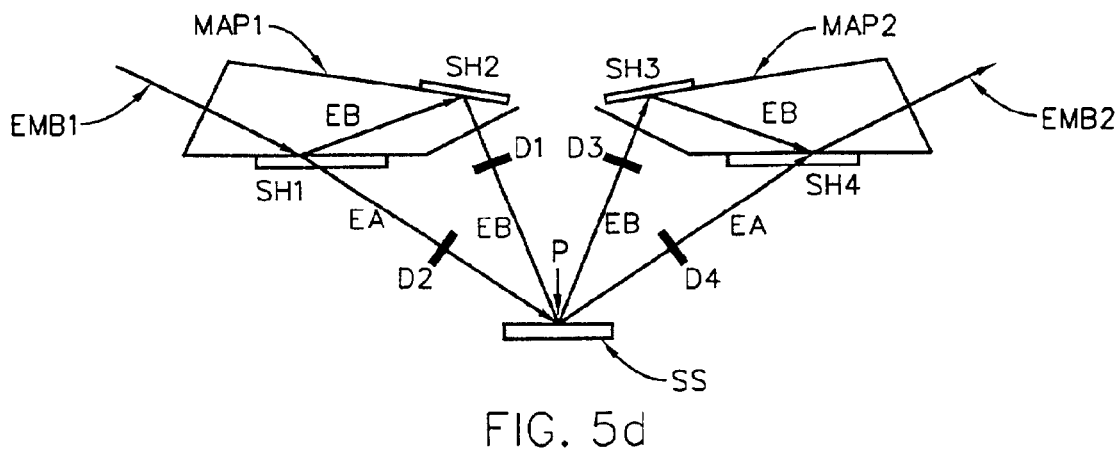
FIG. 5d shows FIG. 5c with door shutters (D1), (D2), (D3) and (D4) present therein.

FIGS. 5c and 5d show additional configurations of Multiple Angle Prisms (MAP1) and (MAP2) which have Shutters (SH1) & (SH2), and (SH3) & (SH4) respectively present thereupon. Said Shutters (SH1) & (SH2), and (SH3) & (SH4) can be, for instance, voltage controlled liquid crystals or electromagnetic-optics means for effectively changing the refractive index of the top and bottom surfaces of a multi-angle prism, for the purpose of controlling the internal reflection/transmission properties. FIG. 5c shows Input Electromagnetic Beam (EMBL) entering Multi-Angle Prism (MAP1) and interacting with the interface between said Multi-Angle Prism (MAP1) and said Shutter (SH1). If said interface is substantially transmissive then Beam (EA) proceeds to the Sample System, and reflects therefrom at point (P). Said Beam (EA) then proceeds through Multi-Angle Prism (MAP2) and exits therefrom as Output Electromagnetic Beam (EMB2). If, however, interface interface between said Multi-Angle Prism (MAP1) and said Shutter (SH1) is substantially reflective, it should be appreciated that Input Electromagnetic Beam (EMB1) will reflect thereat and become beam (EB). It is to be assumed that the interface between said Multi-Angle Prism (MAP1) and said Shutter (SH1) is also substantially reflective, so that beam (EB) continues to reflect from Sample System, and reflects therefrom at point (P), and continue through Multi-Angle Prism (MAP2), wherein it interacts with reflective interfaces between said Multi-Angle Prism (MAP1) and said Shutters (SH3) & (SH4) to emerge as Output Electromagnetic Beam (EMB2).

FIG. 5d shows FIG. 5c with additional Physical Door-Shutter means (D1), (D2), (D3) and (D4) in place to further enhance the Transmision/Reflection effect described with respect to FIG. 5c. For instance, when the interface between Multi-Angle Prism (MAP1) and said Shutter (SH1) is substantially transmissive, Physical Door-Shutter (D2) will be open and Physical Door-Shutter (D1) will be closed. The operation of Said Physical Door-Shutter means (D1), (D2), (D3) and (D4) must, of course, be coordinated with operation of Shutters (SH1) & (SH2), and (SH3) & (SH4), but when present serve to essentially completely overcome the effect of any imperfect operation of Shutters (SH1) & (SH2), and (SH3) & (SH4).

Figure 5E:
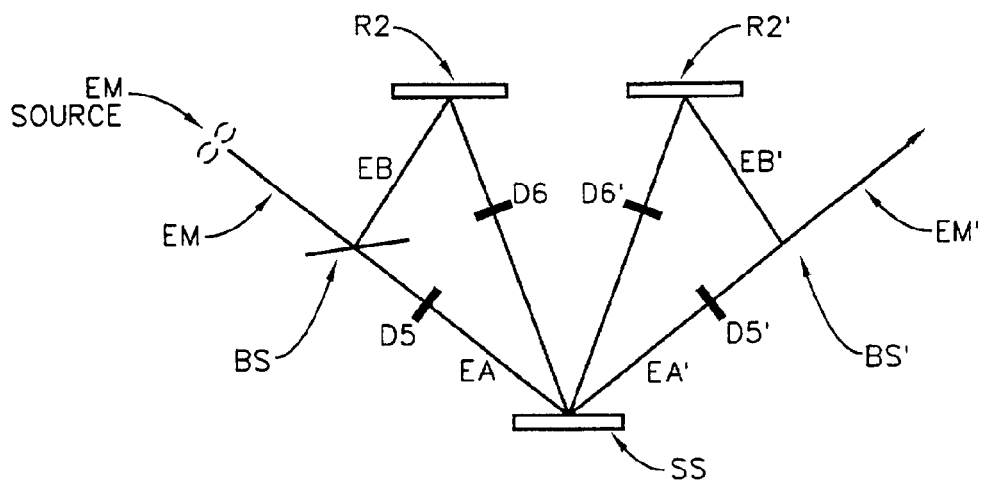
FIG. 5e shows a system for providing multiple angles-of-incidence utilizing Beam Splitter, Reflective means and shutter doors.
Figure 5F:
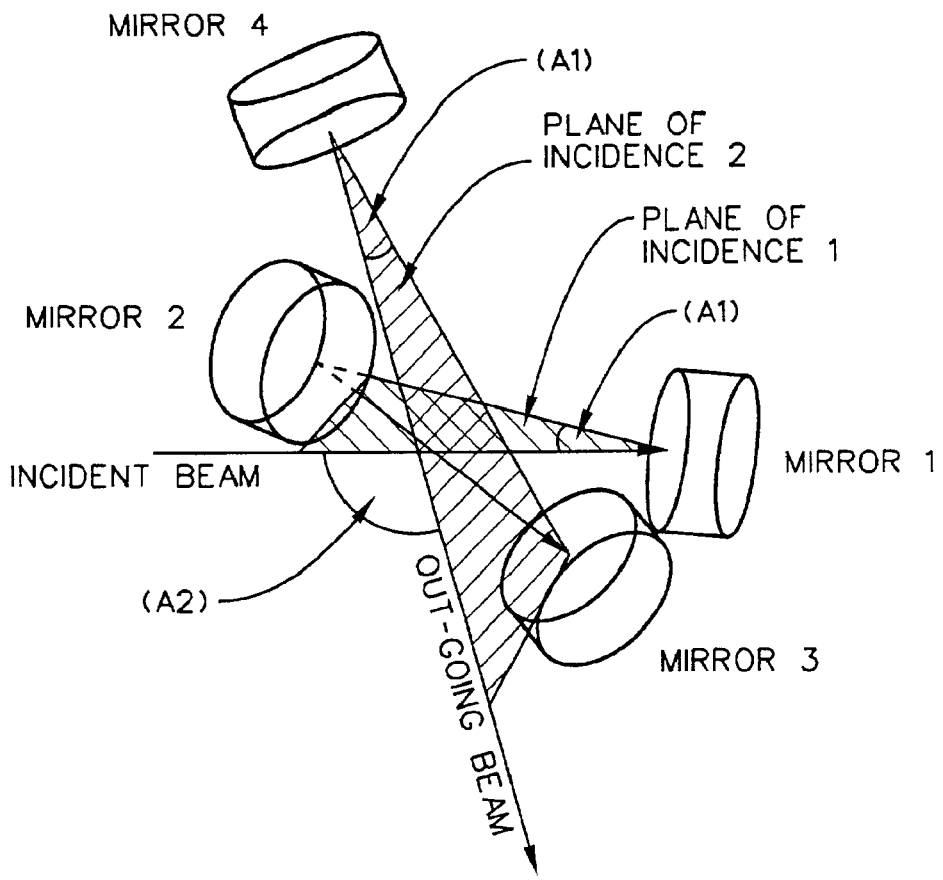
FIG. 5f system is, however, identified as a particularly relevant way to use reflective means to alter the trajectory of a Beam of electromagnetic Radiation, without significantly changing the phase angle between orthogonal components thereof.

FIG. 5e shows an alternative system for effecting different angles of incidence. Note that a Beam Splitter (BS) receives a Beam of Electromagnetic Radiation (EM) and continuously reflects approximately half (EB) and transmits (EA) the remainder. The reflected portion (EB') reflects from a Second Reflection means (R2). Both the reflected (EB') and Transmitted (EA) Electromagnetic Beams arrive at the same point on Sample System (SS), but at different angles-of-incidence. Note, importantly, that Door Shutters (D5) and (D6) are present, and are operated to block one or the other of (EA) and (EB') when desired. After the Sample System (SS), whether it is electromagnetic beam (EA) or (EB') which is allowed to proceed, note that it makes its way to the Detector (DET) by a pathway which is a mirror image to that which brought it to the Sample System (SS) from the Electromagnetic Beam Source. Note that typically four shutter doors (D5) (D6) (D5') (D6') are be present, two on each side of the sample system (SS), said shutter doors being positioned in the loci of the electromagnetic beams which transmit through (EA) and reflect from (EB') the beam splitter (BS) on the incident side of the means for supporting a sample system (SS).

It is important to mention U.S. Pat. No. 5,969,818 to Johs et al. which is incorporated hereinto by reference. Said 818 Patent describes a Beam Folding Optics System which serves to direct an electromagnetic beam via multiple reflections, without significantly changing the phase angle between orthogonal components therein. Briefly, two pairs of mirrors are oriented to form two orthogonally related planes such that the phase shift entered to an electromagnetic beam by interaction with the first pair of mirrors is canceled by interaction with the second pair. The Reflector (R2) in FIG. 5e, (and a similar Reflector in an output side) can comprise Patent 818 Beam Folding Optics. FIG. 5 from said 818 Patent is reproduced herein as FIG. 5f. Note that Beam (EB) in FIG. 5e is shown as is Beam ((EB'), and that Mirrors 1 and 2 form a First Pair, and Mirrors 3 and 4 a Second Pair. Note how the Planes of incidence 1 and 2 are orthogonally related to one another. It is not a focus of Patentability herein to specify any particular FIG. 5e Second Reflective Means (R2) system. The FIG. 5f system is, however, identified as a particularly relevant way to use reflective means to alter the trajectory of a Beam of Electromagnetic Radiation, without significantly changing the phase angle between orthogonal components thereof. Such an effect is similar to that provided by Total Internally Reflective Multi-Angle Prisms, as shown in FIGS. 4, 5a, 5c and 5d herein.

The disclosed invention system also typically includes means for adjusting, for instance, tilt, translation and rotation orientations of the multi-angle prisms and/or the Optional Lenses (OL) within the containing structure. Such presence facilitates easy system set-up optimization. FIG. 6 demonstrates mounting Bases (B1), (B2) and (B3) mounted with respect to one another so that mounting Base (2) can move right and left on mounting Base (1), and so that mounting Base (3) can rotate on mounting Base (2). A Multiangle Prism (MAP) is shown mounted to mounting Base (3). Mounting Base (1) can of course be mounted in a Present Invention Electromagnetic Beam (E) intercepting Angle-of-Incidence (AOI) changing system (1), as shown in FIG. 2, in the position of (BD) or (BD') in a manner to allow it Rotational or any Linear Degrees of Motion Freedom. In particular motion into and out of the plance of the paper is also possible at the (B1), (B2) and/or (B3) level, as required. Note that an Optical Lens (OL) is also shown rotatably and translatably mounted via mounting Base (B4) to mounting Base (1). This is an optional feature, and it is noted that the Optical Lens (OL) can be absent, or separately mounted. FIG. 6 is to be considered only demonstrative, and functional mountings can include any required transalation, tilt and rotation adjustment capability shown, and not directly shown or visible in the view presented.

It is also to be appreciated that while an Electromagnetic Beam. (E) which interacts with a Sample System (SS) will often be polarized, where the disclosed invention system (1) is used with a Reflectometer System, this need not be the case. Reflectometers which produce unpolarized electromagnetic radiation and cause impingement at oblique (AOI's), (instead or in addition thereto ellipsometer produced beams), can have the disclosed invention applied thereto as well.

Figure 7:
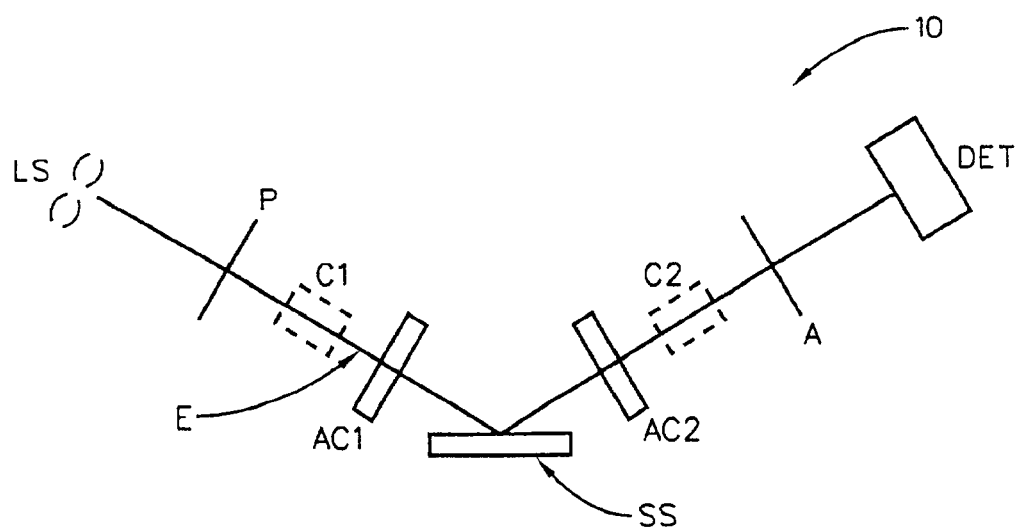
FIG. 7 shows a more detailed presentation of an ellipsometer system to which the Present Invention is applied.

FIG. 7 provides a general elemental configuration of an ellipsometer system (10) which can be applied to investigate a sample system (SS). Shown are, sequentially:

a. a Source of a beam electromagnetic radiation (LS);
  b. a Polarizer element (P);
  c. optionally a compensator element (C1);
  d. (additional element(s)) (AC1);
  e. a sample system (SS);
  f. (additional element(s)) (AC2);
  g. optionally a compensator element (C2);
  h. an Analyzer element (A); and
  i. a Detector System (DET).

It is noted that the elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the disclosed invention Disclosure, input and output electromagnetic beam intercepting angle-of-incidence changing system elements. (Note the presence of indication of an Electromagnetic Beam (E) in FIG. 7, which for orientation it is noted corresponds to the location shown in FIGS. 2, 3a and 3b).

Where, as is generally the case, input (AC1) and output (AC2) additional elements, (eg. multiangle prisms or functional equivalents as represented by (BD) and (ED') in FIG. 2), have bi-refringent characteristics, it must be appreciated that said characteristics must be accounted for in a mathematical model of the ellipsometer and sample system.

FIG. 8 shows a Three-Dimensional view of a disclosed invention system which allows sliding an Angle-Of-Incidence changing system into and out of a beam of electromagnetic radiation in the region a Sample System. Said Drawing is included to provide better insight to physical realization to a disclosed invention embodiment as demonstrated in FIG. 2. Note that the same identifiers are used in FIGS. 2 and 8. Also note that Electromagnetic Beams (E) and (E') are both shown. The designator (E) indicates the beam trajectory when a disclosed (AOI) changing system is moved back along the Translator, and is therefore out of the beam, while (E') shows the beam trajectory when said disclosed (AOI) changing system is moved forward along the Translator into place as shown. Note also that the sample system supporting stage is not shown, but in use would be present to support the shown sample system (SS).

It is to be appreciated that single systems shown FIGS. 5c, 5d, 5e can be fixed in place and various shutters and door shutters operated to effect beam directing. However, multiple embodiments shown in said FIGS. 5c, 5d and 5e can be mounted to a slidable means to enable effecting any of a plurality of angles-of-incidence. Once in place however, two angles-of-incidence can be effected by a FIGS. 5c, 5d or 5e system without physically moving it into an out of a beam of electromagnetic radiation.

It is beneficial at this point to refer to the paper by Johs, titled "Regression Calibration Method for Rotating Element Ellipsometers", which was referenced in the Background Section of this Disclosure. Said paper describes a mathematical regression based approach to calibrating rotating element ellipsometer systems. Said calibration procedure provides that data, (eg. ellipsometric ALPHA and ellipsometric BETA values), be obtained as a function of an ellipsometer system Polarizer Azimuth, as said Polarizer Azimuth is stepped through a range of angles, (eg. sixty (60) degrees to one-hundred-sixty (160) degrees). A mathematical model of the ellipsometer system and a sample system under investigation is provided, and a mathematical square error reducing technique is applied to evaluate parameters in said mathematical model. Successful calibration leads to experimental data and calculated data curves being essentially coincident.

Further insight to the benefit of applying 630 Patent-type regression calibration, and 777 Patent window-like effect corrections to ellipsometer and the like systems which include the disclosed invention multiple-AOI providing system, having then been illuminated herein, can be found in said 630 and 777 Patents which are incorporated by reference in this Specification. Said 777 Patent demonstrates that a methodology for correcting for affects of acquiring ellipsometric data through standard vacuum chamber windows, which can be applied to correcting affects of disclosed invention (AOI) changing systems, has been developed and tested. The key insight enabling said accomplishment is that bi-refringence can be split into "out-of-plane" and "in-plane" components, where the "plane" referred to is the plane of incidence of an electromagnetic beam of radiation with respect to a sample system. Splitting the electromagnetic beam into said orthogonal components allows derivation of second order corrections which were tractable while allowing an ellipsometer system calibration procedure to determine values of parameters. Again, said ellipsometer system calibration procedure allows parameter values in "out-of-plane" component retardation representing equations to be directly evaluated, with the "in-plane" component being an additive factor to a sample system DELTA. A separate step, utilizing a sample system for which retardation can be modeled by a parameterized equation, allows evaluation of the parameters in parametric equations for the "in-plane" components of windows separately. Work reported in the literature by other researchers provided equations which corrected only first order effects, and said equations have proven insufficient to correct for large, (eg. six (6) degrees), of retardation which is typical in standard vacuum chamber windows and which can occur in disclosed invention (AOI) changing systems. It is noted that each total internal reflection in a multiangle prism can impart up to about 45 degrees retardance, depending on the internal reflection angle. Four such bounces can then impart on the order of 160 degrees total phase retardance between the electromagnetic beam orthogonal components.

Continuing to use vacuum chamber windows as example, it is noted that said prior work orthogonal components were derived with respect to window fast axes, which is offset from the sample system plane of incidence). Where the window retardance becomes small, (eg. at longer wavelengths), parameter evaluation in equations for said orthogonal components becomes difficult, as it becomes difficult to determine fast axis orientation. This means that where fast axis orientation can not be identified, algorithm instability becomes a problem. Furthermore, the fast axis orientation of window retardance would also correlate with a sample system DELTA parameter unless a global regression fit using a parameterizable sample system is performed at calibration time. Said methodology comprising two steps as disclosed herein, fully and unambiguously determines correction terms in-situ.

After parameters in parameterized equations for retardance are evaluated by the method of the disclosed invention, ellipsometric data can be taken through disclosed invention (AOI) changing systems and said data can be quickly and accurately analyzed by applying the correction factors in a mathematical model for a sample system, (in the case where a Rotating Analyzer ellipsometer system was used to acquire data), or the (AOI) changing system effects can be simply quantitatively subtracted away to yield "true" ellipsometric PSI and DELTA values, (in the case where a Rotating Compensator ellipsometer system was used to acquire data). Finally, it is noted that the Patent to Johs et al. No. 6,034,777, provides demonstrative data obtained by practice of the described correction methodology as applied to other systems. Said data is incorporated by reference herein and should be considered as demonstrative of results obtained when it is applied to systems including disclosed invention (AOI) changing systems.

It is noted that shutters (SH1) (SH2) (SH3) (SH4) and shutter doors (D1) (D2) (D3) (D4) (D5) (D6) (D5') (D6') can be of any functional type, such as mechanical or voltage driven liquid crystal devices.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A material system investigating system comprising a source of electromagnetic radiation, a means for supporting a sample system, and a detector, such that in use a beam of electromagnetic radiation is provided by said source of electromagnetic radiation and is caused to reflect from a sample system placed on said means for supporting a sample system and enter said detector, said material system investigating system further comprising at least one electromagnetic beam intercepting angle-of-incidence changing system comprising elements which are easily functionally entered into the locus of the electromagnetic beam on both sides of said sample system, which at least one electromagnetic beam intercepting angle-of-incidence changing system serves to direct said electromagnetic beam onto substantially the same spot on the sample system as is the case where the said at least one electromagnetic beam intercepting angle-of-incidence changing system is not functionally present, but at an angle-of-incidence which is different than that when said at least one electromagnetic beam intercepting angle-of-incidence changing system is not functionally present, said at least one electromagnetic beam intercepting angle-of-incidence changing system not effecting, or requiring change of, the locus of the electromagnetic beams outside said at least one electromagnetic beam intercepting angle-of-incidence changing system, on either side of said means for supporting a sample system, hence does not require said material system investigating system to comprise multiple sources and detectors or the change of position of at least one selection from the group consisting of:

said source of electromagnetic radiations and said detector thereof;

to effect change said angle-of-incidence.

2. A material system investigating system as in claim 1, in which said at least one electromagnetic beam intercepting angle-of-incidence changing system comprises, on each side of said means for supporting a sample system, at least one selection from the groups consisting of:

multiple angle prism(s); and a system of mirrors;

said at least one electromagnetic beam intercepting angle-of-incidence changing system being slidably mounted to a guide element such that the functional presence thereof in the pathway of the locus of the electromagnetic beams on both sides of said means for supporting a sample system is effected by physical sliding motion of said at least one electromagnetic beam intercepting angle-of-incidence changing system along said guide element.

3. A material system investigating system as in claim 1, in which said at least one electromagnetic beam intercepting angle-of-incidence changing system comprises a first multiangle prism on the incident side of said means for supporting a sample system and a second multiangle prism thereafter, said first and second multiangle prisms each having a first and a second side, each said multiangle prism presenting with first and second inner surfaces associated with said first and second sides, respectively, the first and second side of each multiangle prism having means for changing the properties of inner surface thereof from essentially transmissive to essentially reflective, each said multiangle prism being oriented such that an electromagnetic beam entering thereinto encounters the first or second inner surface thereof and either passes therethrough and progresses on to contact a sample system placed on said means for supporting a sample system, or reflects from said first or second inner surface thereof and then from said second or first inner surface thereof, respectively, and then progresses on to contact a sample system placed on said means for supporting a sample system.

4. A material system investigating system as in claim 3, which further comprises at least one shutter door which can be opened to let the electromagnetic beam pass, or closed to block its passage, said at least one shutter door being positioned in the electromagnetic beam locus selected from the group consisting of:

defined by passage through said first or second side of said first multiangle prism; and defined by reflection from said first or second side of said first multiangle prism;

said at least one shutter door being positioned between at least one selection from the group consisting of:

said first multiangle prism and the means for supporting a sample system; and said means for supporting a sample system and said second multiangle prism.

5. A material system investigating system as in claim 1, in which said at least one electromagnetic beam intercepting angle-of-Incidence changing system comprises, on first and second sides of said means for supporting a sample system, first and second beam splitters, respectively, which first and second beam splitters each pass approximately half, and reflect approximately half of a beam of electromagnetic radiation caused to be incident thereupon at an oblique angle to a surface thereof; said at least one electromagnetic beam intercepting angle-of-incidence changing system further comprising a first reflective means positioned to intercept the approximately half of the electromagnetic beam which reflects from said first beam splitter on the incident side of said means for supporting a sample system and direct it toward said means for supporting a sample system; and also further comprising a second reflective means positioned after said means for supporting a sample system to intercept an electromagnetic beam which reflects from a sample system placed on said means for supporting a sample system and direct it toward the second beam splitter;

said material system investigating system further comprising at least one shutter door which can be opened to let the electromagnetic beam pass, or closed to block its passage, said at least one shutter door being positioned in the pathway of the electromagnetic beam between which progresses along a locus selected from the group consisting of:

defined by passage through said first beam splitter; and defined by reflection from said first beam splitter;

on either side of said means for supporting a sample system.

6. A material system investigating system as in claim 1 or 2 or 3 or 4 or 5 which is a system selected from the group consisting of:

ellipsometer;

polarimeter;

reflectometer; and spectrophotometer;

operating in at least one wavelength range selected from the group consisting of:

VUV;

UV;

Visible;

Infrared;

Far Infrared;

Radio Wave;

and is applied in a setting selected from the group consisting of:

in-situ; and ex-situ.

7. A material system Investigating system as in claim 1 or 2 or 3 or 4 or 5 in which said material system Investigating system is mounted to an X-Y-Z position control system, and which is oriented to investigate a surface of a sample system oriented in a horizontal or vertical or a plane thereinbetween.

8. A material system Investigating system as in claim 1, which includes at least two multiple angle prisms, one being present on one side of said sample system, and the other thereof being present on the other side of said sample system.

9. A material system investigating system as in claim 1, which includes lenses positioned to focus a beam of electromagnetic radiation onto a sample system.

10. A material system investigating system as in claim 1, which includes means for adjusting the orientation of at least one electromagnetic beam intercepting angle-of-incidence changing system, optionally in simultaneous combination which includes lenses positioned to focus a beam of electromagnetic radiation onto a sample system and recollimate the beam of electromagnetic radiation which reflects from said sample system.

11. A material system investigating system as in claim 1, in which the at least one electromagnetic beam intercepting angle-of-incidence changing system comprises, on at least one side selected from the group consisting of:

said first and;

said second;

sides of said means for supporting a sample system, at least one system of mirrors, said at least one system of mirrors being comprised of:

a means for changing the propagation direction of an initial beam of electromagnetic radiation without significantly changing the phase angle between orthogonal components thereof, said means comprising two pairs of reflecting mirrors oriented so that said initial beam of electromagnetic radiation reflects from a first reflecting means in the first pair of reflecting means to a second reflecting means in said first pair of reflecting means, in a first plane; and such that the beam of electromagnetic radiation which reflects from the second reflecting means in said first pair of reflecting means reflects from the first reflecting means in said second pair of reflecting means to said second reflecting means in said second pair of reflecting means, in a second plane which is essentially orthogonal to said first plane; such that the direction of propagation of the beam of electromagnetic radiation reflected from the second reflecting means in said second pair of reflecting means is different from the propagation direction of the initial beam of electromagnetic radiation; the basis of operation being that changes entered between the orthogonal components by the first pair of reflective means is canceled by that entered by the second pair of reflective means.

12. A method of calibrating a material system investigation system comprising the steps of:

a. providing a material system investigation system comprising a source of a polychromatic beam of electromagnetic radiation, a polarizer, a stage for supporting a sample system, an analyzer, a dispersive optics and at least one detector system which contains a multiplicity of detector elements, said material system investigation system optionally comprising at least one compensator (s) positioned at a location selected from the group consisting of:

before said stage for supporting a sample system; and
after said stage for supporting a sample system; and
both before and after said stage for supporting a sample system;

such that when said material system investigation system is used to investigate a sample system present on said stage for supporting a sample system, at least one selection from the group consisting of:

said analyzer;
said polarizer; and
at least one of said at least one compensators);

is/are caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said sample system, pass through said analyzer and interact with said dispersive optics such that a multiplicity of essentially single wavelengths are caused to simultaneously enter a corresponding multiplicity of detector elements in said at least one detector system;

said material system investigating system further comprising at least one angle-of-incidence changing system which is easily functionally entered into the locus of the electromagnetic beam on both sides of said means for supporting a sample system, which at least one angle-of-incidence changing system serves to direct said electromagnetic beam onto substantially the same spot on the sample system as is the case where the said at least one angle-of-incidence changing system is not present, but at an angle-of-incidence which is different when said at least one angle-of-incidence changing system is and is not functionally present, said at least one angle-of-incidence changing system not effecting, or requiring change of, the locus of the electromagnetic beams outside said at least one angle-of-incidence changing system, on either side of said means for supporting a sample system, hence does not require multiple sources and detectors or change of position of at least one selection from the group consisting of:

said source of electromagnetic radiation; and said detector thereof;
to effect change said angle-of-incidence;

b. along with step a., developing a mathematical model of said material system investigation system which comprises as calibration parameter variables selections from the group consisting of:

polarizer azimuthal angle orientation;
present sample system PSI;
present sample system DELTA;
compensator azimuthal angle orientation(s);
matrix components of said compensator(s); and
analyzer azimuthal angle orientation;
angle-of-incidence changing system representation;

which mathematical model is effectively a transfer function which enables calculation of electromagnetic beam intensity as a function of wavelength detected by a detector element, given intensity as a function of wavelength provided by said source of a polychromatic beam of electromagnetic radiation;

c. causing a polychromatic beam of electromagnetic radiation produced by said source of a polychromatic beam of electromagnetic radiation, to pass through said polarizer, interact with a sample system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through present compensator(s);

d. obtaining an at least two dimensional data set of intensity values vs. wavelength and a parameter selected from the group consisting of:

angle-of-incidence of said polychromatic beam of electromagnetic radiation with respect to a present sample system, and
azimuthal angle rotation of at least one element selected from the group consisting of:
said polarizer; and
said analyzer;
at least one of said at least one compensator(s);
while at least one selection from the group consisting of
said polarizer; and
said analyzer;
at least one of said at least one compensator(s);
is caused to continuously rotate;

e. performing a mathematical regression of said mathematical model onto said at least two dimensional data set, thereby evaluating calibration parameters in said mathematical model;

said regression based calibration procedure evaluated calibration parameters serving to compensate said mathematical model for non-achromatic characteristics and non-idealities of said compensator(s), and for azimuthal angles of said polarizer, analyzer and compensator(s) and for said angle-of-incidence changing system.

13. A method of calibrating a material system investigation system investigation system as in claim 12 which further comprises including at least one selection from the group consisting of:

calibration parameters for detector element image persistence; and
read-out nonidealities in the mathematical model;
and further evaluating said calibration parameters for detector element image persistence and read-out nonidealities in said regression procedure.

14. A method of calibrating a material system investigation system as in claim 12 in which the step of developing a calibration parameter containing mathematical model thereof includes the steps of providing a matrix representation of each of said polarizer, present sample system, said compensator(s), and said analyzer, and determining a mathematical transfer function relating electromagnetic beam intensity out to intensity in, as a function of wavelength, by multiplication of said matrices in a spectroscopic rotating element material system investigation system element presence representing order.

15. A method of calibrating a material system investigation system as in claim 12, which further comprises the step of parameterizing calibration parameters by representing variation as a function of at least one member of the group consisting of:

wavelength;

angle-of-incidence of said polychromatic beam of electromagnetic radiation with respect to a present sample system, sample system characterizing parameters; and azimuthal angle orientation of one element selected from the group consisting of:

said polarizer; and said analyzer;

by a parameter containing mathematical equation, said parameters being evaluated during said mathematical regression.

16. A method of calibrating a material system investigation system as in claim 15, in which calibration parameters which are parameterized are selected from the group consisting of:

polarizer azimuthal angle orientation;

compensator azimuthal angle orientation(s);

matrix components of said compensator(s), and analyzer azimuthal angle orientation;

each as a function of wavelength.

17. A method of calibrating a material system investigation system as in claim 12 in which the sample system is selected from the group consisting of:

open atmosphere with the spectroscopic rotating compensator material system investigation system being oriented in a "straight-through" configuration; and other than open atmosphere with the spectroscopic rotating compensator material system investigation system being oriented in a "sample-present" configuration.

18. A sample system investigation system for application in investigating a sample system with electromagnetic radiation, sequentially comprising:

a. a source of a beam electromagnetic radiation;

b. a polarizer element;

c. optionally a compensator element;

d. additional element(s);

e. a sample system;

f. additional element(s);

g. optionally a compensator element;

h. an Analyzer element; and i. a Detector System;

wherein said additional component(s) in d. and f. each comprise at least one electromagnetic beam intercepting angle-of-incidence changing system element which can be easily entered into the locus of the electromagnetic beam on both sides of said sample system, which at least one electromagnetic beam intercepting angle-of-incidence changing system elements serves to direct said electromagnetic beam onto substantially the same spot on the sample system as is the case where the said at least one electromagnetic beam intercepting angle-of-incidence changing system elements are not present, but at an angle-of-incidence which is different than that when said at least one electromagnetic beam intercepting angle-of-incidence changing system is not present, said at least one electromagnetic beam intercepting angle-of-incidence changing system elements not effecting, or requiring change of, the locus of the electromagnetic beams outside said at least one electromagnetic beam intercepting angle-of-Incidence changing system elements, on either side thereof, hence does not require multiple sources and detectors or change of position of at least one selection from the group consisting of:

said source of electromagnetic radiation; and said detector thereof;

to effect change said angle-of-incidence.

19. A sample system investigation system for application in investigating a sample system with electromagnetic radiation as in claim 18, in which each electromagnetic beam intercepting angle-of-incidence changing system is a selection from the group consisting of:

multiangle prisms; and a plurality of mirrors.

* * * * *